United States Patent
Martin et al.

(10) Patent No.: US 12,252,582 B2
(45) Date of Patent: Mar. 18, 2025

(54) BIOFUNCTIONAL THIOPHENE MONOMERS AND POLYMERS THEREOF FOR ELECTRONIC BIOMEDICAL DEVICES

(71) Applicants: David C. Martin, Lincoln University, PA (US); Samadhan Suresh Nagane, Maharashtra (IN); Peter Sitarik, Fleetwood, PA (US)

(72) Inventors: David C. Martin, Lincoln University, PA (US); Samadhan Suresh Nagane, Maharashtra (IN); Peter Sitarik, Fleetwood, PA (US)

(73) Assignee: University Of Delaware, Newark, DE (US)

( * ) Notice: Subject to any disclaimer, the term of this patent is extended or adjusted under 35 U.S.C. 154(b) by 0 days.

(21) Appl. No.: 17/637,108

(22) PCT Filed: Aug. 28, 2020

(86) PCT No.: PCT/US2020/048495
§ 371 (c)(1),
(2) Date: Feb. 22, 2022

(87) PCT Pub. No.: WO2021/041874
PCT Pub. Date: Mar. 4, 2021

(65) Prior Publication Data
US 2022/0289902 A1    Sep. 15, 2022

Related U.S. Application Data

(60) Provisional application No. 62/893,248, filed on Aug. 29, 2019.

(51) Int. Cl.
*C08G 61/12* (2006.01)
*C07D 495/04* (2006.01)
(Continued)

(52) U.S. Cl.
CPC ......... *C08G 61/126* (2013.01); *C07D 495/04* (2013.01); *C07D 519/00* (2013.01);
(Continued)

(58) Field of Classification Search
CPC ............... C08G 61/126; C08G 61/123; C08G 2261/122; C08G 2261/1424;
(Continued)

(56) References Cited

U.S. PATENT DOCUMENTS 5,834,290 A    11/1998   Egelrud et al.
7,708,908 B2 *  5/2010   Kim ..................... C07D 495/04
                                                   252/500
(Continued)

FOREIGN PATENT DOCUMENTS

AU    2013267009 A1    1/2014
EP       2437061 A1    4/2012
(Continued)

OTHER PUBLICATIONS

Bigeleisen, P., "Nerve Puncture and Apparent Intraneural Injection during Ultrasound-guided Axillary Block Does Not Invariably Result in Neurologic Injury", Anesthesiology, 2006, 105:779-83.
(Continued)

*Primary Examiner* — Shane Fang
(74) *Attorney, Agent, or Firm* — BUCHANAN INGERSOLL & ROONEY PC

(57) ABSTRACT

The functionalized 3,4-alkylenedioxythiophene (ADOT+) monomers can be represented by a chemical formula $(CR^1R^2)(CR^3R^4)(CR^4R^5)_xO_2C_4H_2S$, wherein x=0 or 1; wherein each of $R^1$, $R^2$, $R^3$, $R^4$, $R^5$, and $R^6$ is independently selected from hydrogen, a hydrocarbyl moiety, and a heteroatom-containing functional group; and wherein at least one of $R^1$, $R^2$, $R^3$, $R^4$, $R^5$, and $R^6$ comprises the heteroatom-containing functional group selected from an aldehyde, a
(Continued)

maleimide, and their derivatives thereof. Also, disclosed herein are aldehyde derivatives represented by (ADOT-CH$_2$—NH)$_p$Y and a maleimide derivative represented by (ADOT-(CH$_2$)$_q$—N)$_p$Z where p=1-2 and each of Y and Z is a hydrocarbyl moiety or a biofunctional hydrocarbyl moiety. In an embodiment of the ADOT+ monomers, one of R$^1$, R$^2$, R$^3$, R$^4$, R$^5$, and R$^6$ is replaced by a direct bond to an amide group, an azide group, or an ester group of a biofunctional hydrocarbyl moiety. Also, disclosed herein are polymers and copolymers made therefrom.

11 Claims, 10 Drawing Sheets

(51) Int. Cl.
   C07D 519/00 (2006.01)
   C07J 33/00 (2006.01)
   H01B 1/12 (2006.01)
(52) U.S. Cl.
   CPC ............ *C07J 33/002* (2013.01); *H01B 1/124* (2013.01); *C08G 2261/122* (2013.01); *C08G 2261/1424* (2013.01); *C08G 2261/1426* (2013.01); *C08G 2261/1428* (2013.01); *C08G 2261/1432* (2013.01); *C08G 2261/148* (2013.01); *C08G 2261/334* (2013.01); *C08G 2261/44* (2013.01); *C08G 2261/94* (2013.01)
(58) Field of Classification Search
   CPC .... C08G 2261/1426; C08G 2261/1428; C08G 2261/1432; C08G 2261/148; C08G 2261/334; C08G 2261/44; C08G 2261/94; C07D 495/04; C07D 519/00; C07J 33/002; H01B 1/124; C09K 9/02; C09K 2211/1491; C09K 2211/1483; C09K 2211/1458; C09K 2211/1466; C09K 2211/145; C09K 2211/1425; C09K 2211/1416
   See application file for complete search history.

(56) References Cited

U.S. PATENT DOCUMENTS

| | | |
|---|---|---|
| 7,767,414 B1 | 8/2010 | Smith et al. |
| 8,006,526 B2 | 8/2011 | Martin et al. |
| 8,114,662 B2 | 2/2012 | Clark et al. |
| 8,145,434 B2 | 3/2012 | Shachar et al. |
| 8,263,358 B2 | 9/2012 | Clark et al. |
| 8,571,805 B2 | 10/2013 | Shachar et al. |
| 8,586,702 B2 | 11/2013 | Martin et al. |
| 8,936,794 B2 | 1/2015 | Martin et al. |
| 2001/0023078 A1 | 9/2001 | Bawendi et al. |
| 2002/0176084 A1 | 1/2002 | Garini et al. |
| 2003/0013094 A1 | 1/2003 | Weiner et al. |
| 2003/0152517 A1 | 8/2003 | Peyman |
| 2003/0157483 A1 | 8/2003 | Sorge et al. |
| 2003/0162216 A1 | 8/2003 | Gold et al. |
| 2003/0215864 A1 | 11/2003 | Gilmanshin et al. |
| 2004/0009612 A1 | 1/2004 | Zhao et al. |
| 2004/0053399 A1 | 3/2004 | Gilmanshin |
| 2004/0167625 A1 | 8/2004 | Beyar et al. |
| 2004/0227128 A1 | 11/2004 | Reuter et al. |
| 2004/0248144 A1 | 12/2004 | Mir |
| 2005/0003386 A1 | 1/2005 | Bazan et al. |
| 2005/0013094 A1 | 1/2005 | Reuter et al. |
| 2005/0123974 A1 | 6/2005 | Gilmanshin et al. |
| 2005/0216313 A1 | 9/2005 | Claud et al. |
| 2005/0260684 A1 | 11/2005 | van Dongen |
| 2005/0266067 A1 | 12/2005 | Sengupta et al. |
| 2006/0014315 A1 | 1/2006 | Chan et al. |
| 2006/0024722 A1 | 2/2006 | Fischer-Colbrie et al. |
| 2006/0046260 A1 | 3/2006 | Kriksunov et al. |
| 2006/0078490 A1 | 4/2006 | Shih et al. |
| 2006/0099148 A1 | 5/2006 | Fisher et al. |
| 2006/0107277 A1 | 5/2006 | Guo et al. |
| 2006/0134001 A1 | 6/2006 | Frangioni |
| 2006/0148103 A1 | 7/2006 | Chen et al. |
| 2006/0173362 A1 | 8/2006 | Toms et al. |
| 2006/0183247 A1 | 8/2006 | Kim et al. |
| 2006/0228367 A1 | 10/2006 | Chng et al. |
| 2007/0028928 A1 | 2/2007 | Peyman |
| 2007/0072220 A1 | 3/2007 | Chilkoti |
| 2007/0086842 A1 | 4/2007 | Chang et al. |
| 2007/0111324 A1 | 5/2007 | Nie et al. |
| 2007/0148645 A1 | 6/2007 | Hoser |
| 2007/0154881 A1 | 7/2007 | Koo |
| 2007/0219367 A1 | 9/2007 | Shchepinov et al. |
| 2007/0231790 A1 | 10/2007 | Su |
| 2008/0050513 A1 | 2/2008 | Wang et al. |
| 2008/0057497 A1 | 3/2008 | Filanoski et al. |
| 2008/0103116 A1 | 6/2008 | Jennings-Spring |
| 2008/0159842 A1 | 7/2008 | Kang et al. |
| 2008/0212866 A1 | 9/2008 | Lett et al. |
| 2008/0213177 A1 | 9/2008 | Rademacher et al. |
| 2008/0224099 A1 | 9/2008 | Kim et al. |
| 2008/0268462 A1 | 10/2008 | Kosmeder et al. |
| 2008/0274463 A1 | 11/2008 | Chen et al. |
| 2008/0305497 A1 | 12/2008 | Kosmeder et al. |
| 2008/0317768 A1 | 12/2008 | Bianchi |
| 2009/0075881 A1 | 3/2009 | Catelas et al. |
| 2009/0123366 A1 | 5/2009 | Yang et al. |
| 2009/0123931 A1 | 5/2009 | McNulty et al. |
| 2009/0127113 A1 | 5/2009 | Chen et al. |
| 2009/0131360 A1 | 5/2009 | Woolf et al. |
| 2009/0156673 A1 | 6/2009 | Zharov |
| 2009/0220130 A1 | 9/2009 | Slingerland |
| 2009/0238229 A1 | 9/2009 | Weaver et al. |
| 2010/0015594 A1 | 1/2010 | Poetter et al. |
| 2010/0021957 A1 | 1/2010 | Lin et al. |
| 2010/0130367 A1 | 5/2010 | Murthy et al. |
| 2010/0136614 A1 | 6/2010 | Luo et al. |
| 2010/0143666 A1 | 6/2010 | Mirkin et al. |
| 2010/0167294 A1 | 7/2010 | Huang et al. |
| 2010/0168390 A1 | 7/2010 | Brix et al. |
| 2010/0184681 A1 | 7/2010 | Eckert et al. |
| 2010/0202870 A1 | 8/2010 | Zhang et al. |
| 2010/0209353 A1 | 8/2010 | Kwon et al. |
| 2010/0301855 A1 | 12/2010 | Hyde et al. |
| 2010/0316643 A1 | 12/2010 | Eckert et al. |
| 2011/0003710 A1 | 1/2011 | Konstantopoulos et al. |
| 2011/0165647 A1 | 7/2011 | Fernig et al. |
| 2011/0236411 A1 | 9/2011 | Scholler et al. |
| 2011/0237000 A1 | 9/2011 | Tey et al. |
| 2011/0256528 A1 | 10/2011 | Poetter et al. |
| 2011/0294117 A1 | 12/2011 | Kim et al. |
| 2011/0311505 A1 | 12/2011 | Ersoz et al. |
| 2011/0313380 A1 | 12/2011 | Brix et al. |
| 2012/0003632 A1 | 1/2012 | Van Dongen et al. |
| 2012/0023620 A1 | 1/2012 | Yau et al. |
| 2012/0027689 A1 | 2/2012 | Blanchard et al. |
| 2012/0040397 A1 | 2/2012 | Luo et al. |
| 2012/0076831 A1 | 3/2012 | Miller et al. |
| 2012/0088232 A1 | 4/2012 | Wanekaya et al. |
| 2012/0141767 A1 | 6/2012 | Chen-Yang et al. |
| 2012/0178893 A1 | 7/2012 | Martin et al. |
| 2012/0258870 A1 | 10/2012 | Schwartz et al. |
| 2012/0270231 A1 | 10/2012 | Smith et al. |
| 2012/0270235 A1 | 10/2012 | Kim et al. |
| 2012/0295368 A1 | 11/2012 | Im et al. |
| 2012/0301872 A1 | 11/2012 | Tormod |
| 2012/0301886 A1 | 11/2012 | Farrell et al. |
| 2012/0329708 A1 | 12/2012 | DiMarchi et al. |
| 2013/0005026 A1 | 1/2013 | Gombrich et al. |
| 2013/0029356 A1 | 1/2013 | Stilwell |
| 2013/0034863 A1 | 2/2013 | Papazoglou et al. |
| 2013/0039848 A1 | 2/2013 | Bradbury et al. |
| 2013/0053641 A1 | 2/2013 | Shankar et al. |
| 2013/0109019 A1 | 5/2013 | Murillo et al. |
| 2013/0116172 A1 | 5/2013 | DiMarchi et al. |
| 2013/0115674 A1 | 6/2013 | Sutkowski et al. |

(56) References Cited

U.S. PATENT DOCUMENTS

| | | |
|---|---|---|
| 2013/0289253 A1 | 10/2013 | Luescher et al. |
| 2013/0315831 A1 | 11/2013 | Shi et al. |
| 2013/0337471 A1 | 12/2013 | Nie et al. |
| 2013/0344508 A1 | 12/2013 | Schwartz et al. |
| 2014/0006517 A1 | 1/2014 | Hsiao et al. |
| 2014/0010886 A1 | 1/2014 | Wilson et al. |
| 2014/0048776 A1 | 2/2014 | Huang et al. |
| 2014/0093979 A1 | 4/2014 | Papazoglou et al. |
| 2014/0141452 A1 | 5/2014 | Watt et al. |
| 2014/0186824 A1 | 7/2014 | Burdick et al. |
| 2014/0219915 A1 | 8/2014 | Smith et al. |
| 2014/0227723 A1 | 8/2014 | Ingber et al. |
| 2014/0256034 A1 | 9/2014 | Chung et al. |
| 2014/0302516 A1 | 10/2014 | Chiu et al. |
| 2014/0336071 A1 | 11/2014 | Salaita et al. |
| 2014/0350183 A1 | 11/2014 | Chiu et al. |
| 2015/0005188 A1 | 1/2015 | Levner et al. |
| 2015/0141268 A1 | 6/2015 | Rothberg et al. |
| 2015/0202299 A1 | 7/2015 | Burdick et al. |
| 2015/0218252 A1 | 8/2015 | Ingber et al. |
| 2015/0323530 A1 | 11/2015 | Wang |
| 2015/0337061 A1 | 11/2015 | Yano et al. |
| 2015/0343060 A1 | 12/2015 | Kovar et al. |
| 2016/0331941 A1 | 2/2016 | Eckert et al. |
| 2016/0344937 A1 | 11/2016 | Iwashita et al. |
| 2020/0157360 A1 | 5/2020 | Lin et al. |

FOREIGN PATENT DOCUMENTS

| | | |
|---|---|---|
| EP | 2629095 A1 | 8/2013 |
| WO | 2006001848 A2 | 1/2006 |
| WO | 2006107617 A2 | 10/2006 |
| WO | 2006107786 A2 | 10/2006 |
| WO | 2007046893 A2 | 4/2007 |
| WO | 2007057428 A1 | 5/2007 |
| WO | 2007092713 A2 | 8/2007 |
| WO | 2008130326 A1 | 10/2008 |
| WO | 2008147456 A2 | 12/2008 |
| WO | 2008156460 A1 | 12/2008 |
| WO | 2009106073 A2 | 9/2009 |
| WO | 2010037397 A1 | 4/2010 |
| WO | 2011017691 A2 | 2/2011 |
| WO | 2011045394 A1 | 4/2011 |
| WO | 2016006374 A1 | 1/2015 |
| WO | 2015047396 A1 | 4/2015 |
| WO | 2015055708 A1 | 4/2015 |
| WO | 2015080670 A1 | 6/2015 |
| WO | 2015095603 A1 | 6/2015 |
| WO | 2015095604 A2 | 6/2015 |
| WO | 2016007919 A2 | 1/2016 |

OTHER PUBLICATIONS

Birch et al., "Age-related macular degeneration; a target for Nanotechnology derived medicines", Int. J. Nanomedicine 2007, 2 (1), 65, 14 pages.

Braiek et al., "An Electrochemical Immunosensor for Detection of *Staphylococcus aureus* Bacteria Based on Immobilization of Antibodies on Self-Assembled Monolayers-Functionalized Gold Electrode", Biosensors 2012. 2 (4), 417-426.

Daniels et al., "Label-Free Impedance Biosensors: Opportunities and Challenges", Electroanalysis 2007, 19 (12). 1239-1257.

Dean et al., "Electrical Impedance Spectroscopy Study of Biological Tissues", J. Electrostat. 2008, 66 (3-4), 165-177.

Dutta et al., "Impedance spectroscopy studies on Ga-ion-modified PLZT ceramics", Phys, Status Solidi A 2005, 202 (6), 1172-1181.

Emerson et al., "Current and emerging therapies for the treatment age-related macular degeneration", Clinical, Ophthalmology 2008, 2 (2), 377-388.

Ferrara, N., "Vascular Endothelial Growth Factor: Basic Science and Clinical Progress", Endocrine Reviews 2004, 25 (4), 581-611.

Hayat et al., "Disposable Screen Printed Electrochemical Sensors: Tools for Environmental Monitoring", Sensors 2014, 14 (6), 10432-10453.

Jager et al., "Age-related Macular Degeneration", N. Engl. J. Med. 2008, 358 (24), 2606-2617.

Kara et al., "Aptamers based electrochemical biosensor for protein detection using carbon nanotubes platforms", Biosensors and Bioelectronics 2010, 26 (4), 1715-1718.

Maguire, M. G., "Companng Treatments for Age-Related Macular Degeneration: Safety, Effectiveness and Cost", Leonard Davis Institute of Health Economics Issue Brief 2012, 17 (8), 1-4.

Mishra et al., "On-chip micro-biosensor for the detection of human CD4+ cells based on AC impedance and optical analysis", Biosensors and Bioelectronics 2005, 21 (5), 696-704.

Nagane et al., "Functionalized Polythiophene Copolymers for Electronic Biomedical Devices", downloaded from https://www.cambridge.org/core, on Apr. 29, 2020, 14 pages.

Park et al., "DNA Hybridization Sensors Based on electrochemical Impedance Spectroscopy as a Detection Tool", Sensors 2009, 9 (12), 9513-9532.

Park et al., "Redox-active charge carriers of conducting polymers as a tuner of conductivity and its potential window", Scientific Reports 2013, 3, 2454.

Rakic et al., "Placental Growth Factor, a Member of the VEGF Family, Contributes to the Development of Choroidal Neovascularization", Investigative Opthalmology & Visual Science 2003, 44 (7), 3186-3193.

Singh et al., "Nanoparticle-enhanced sensitivity of a nanogap-interdigitated electrode array impedimetric biosensor", Langmuir 2011, 27 (22), 13931-13939.

Spichiger-Keller, U. E., "Chemical sensors and biosensors for medical and biological applications", Wiley-VCH: Weinheim; New York; Chichester; Brisbane; Singapore; Toronto, 1998, 30 pages.

Suni, I., "Impedance methods for electrochemical sensors using nanomaterials", Trends in Analytical Chemistry 2008, 27 (7), 604-611.

Wang et al., "Design and Analysis of a PZT-Based Micromachined Acoustic Sensor with Increased Sensitivity", IEEE Transactions on Ultrasonics Ferroelectrics, and Frequency Control 2005, 52 (10), 1840-1850.

International Preliminary Report on Patentability for International Application No. PCT/US2020/048495, dated Mar. 1, 2022, 9 pages.

International Search Report and Written Opinion for International Application No. PCT/US2020/048495, dated Dec. 2, 2020, 11 pages.

Adamis et al., "The Role of Vascular Endothelial Growth Factor in Ocular Health and Disease", Retina, 2005, 25 (2), 111-118.

Dietrich et al., "Electrochemical and spectroscopic characterization polyalkylenedioxythiophenes", Journal of Electroanalytical Chemistry, vol. 369, pp. 87-92.

Hai et al., "Specific Recognition of Human Influenza Virus with PEDOT Bearing Sialic Acid-Terminated Trisaccharrides", ACS Applied Materials & Interfaces, 2017, 9(16): 14162-70.

Hakkinen, H., "The gold-sulfur interface at the nanoscale", Nature Chemistry 2012, 4 (6), 443-465.

Howell et al., "Composition of Vinylidene Chloride/Phenylacetylene (VDC /PA) Copolymers and Vinylidene Chloride/Methyl Acrylate/ Phenylacetylene (VDS/MA/PA) Terpolymers from Analysis by 130-NMR Spectroscopy", J. Polymer Science Part B, Polymer Chemistry, vol. 26, pp. 1287-1294 (1988).

Kharitonov et al., "Probing of bioaffinity interactions at interfaces using impedance spectroscopy and chronopotentiometry", J. Electroanalytical Chemistry 2000, 487 (2), 133-141.

Kim et al., "A Single-Step Synthesis of Electroactive Mesoporous ProDOT-Silica Structures," Angewandte Chemie International Edition 2015, 127 (29): 8527-8530.

Kovacic et al., "Polymerization of Benzene to p-Polyphenyl by Aluminum Chloride-Cupric Chloride1", Journal of the American Chemical Society, vol. 85, pp. 454-458 (1963).

(56) References Cited

OTHER PUBLICATIONS

Li et al., "Nano Chemical Sensors With Polymer-Coated Carbon Nanotubes", IEEE Sensors Journal 2006, 6 (5), 1047-1051.

Min et al., "Characterization and Optimization of Interdigitated Ultramicroelectrode Arrays as Electrochemical Biosensor Transducers", Electroanalysis 2004, 16 (9), 724-729.

Miriani et al., "Cytotoxic Analysis of the Conducting Polymer PEDOT using Myocytes", IEEE, 2008; pp. 1841-1844.

Pan et al., "Electrochemical sensors of octylphenol based on molecularly imprinted poly(3,4-ethylenenedioxythophene) and poly(3,4-ethylenedioxythiophene-gold nanoparticles)", RSC Adv 2015, 5 (71), 57671-57677.

Potyrailo et al., "Introduction to Combinatorial methods for chemical and biological sensors; Integrated analytical systems", Springer: New York, NY, 2009, 22 pages.

Radke et al., "Design and Fabrication of a Microimpedance Biosensor for Bacterial Detection", IEEE Sensors J. 2004, 4 (4), 434-440.

Sharifi-Viand et al., "Investigation of anomalous diffusion and multifractal dimensions in polypyrrole film", J Electroanalytical Chemistry 2012, 671, 51-57.

Smiechowski et al. "Electrochemical detection and characterization of proteins", Biosensors and Bioelectronics 2006, 22 (5), 670-677.

Yang et al., "The voltammetric performance of interdigitated electrodes with different electron-transfer rate constants", Sensors and Actuators B Chem. 2007, 126 (2) 624-631.

Gordon, S., "The aging eye", Fireside: Simon and Schuster, New York, 2001, 10 pages.

Elschner et al., "PEDOT: Principles and Applications an Intrinsically Conductive Polymer", CRC Press, 2011, 41 pages.

Inzelt, G., "Conducting polymers: A New Era in Electrochemistry", 2nd ed.; Monographs in electrochemistry; Springer; Heidelberg: New York, 2012, 48 pages.

Povlich et al., "Carboxylic Acid-modified Edot for Biofunctionalization of Neural Probe Electrodes", Proceedings Published by the American Chemical Society, 2007, 2 pages.

Extended European Search Report for European Application No. 20050049.1, dated Jul. 18, 2023, 11 pages.

\* cited by examiner

BIOFUNCTIONAL THIOPHENE MONOMERS AND POLYMERS THEREOF FOR ELECTRONIC BIOMEDICAL DEVICES

CROSS-REFERENCE TO RELATED APPLICATIONS

This application is a national stage application under 35 U.S.C. § 371 of International Application No. PCT/US2020/048495, filed Aug. 28, 2020, which claims priority to U.S. Provisional Patent Application No. 62/893,248 filed Aug. 29, 2019, the entire disclosures of each of these applications being incorporated herein by reference for all purposes.

STATEMENT REGARDING FEDERALLY SPONSORED RESEARCH

This invention was made with government support under Grant No. HR0011-17-2-0019 awarded by the Defense Advanced Research Projects Agency (DARPA) and Grant No. DMR-1808048 awarded by the National Science Foundation/Division of Materials Research. The government has certain rights in the invention.

BACKGROUND OF THE INVENTION

Functionalized polythiophene copolymers based on alkyldithiophenes, particularly poly(3,4-ethylene dioxythiophene) (PEDOT), have become the standard for use in biomedical electronic devices as well as other applications including photovoltaics and chemical sensors. PEDOT copolymers have good mechanical properties, thermal stability, and chemical stability, making them attractive for use in these applications. PEDOT doped with poly(4-styrene sulfonate) (PSS) is commercially available in a processable aqueous suspension for fabricating organic electronic devices at relatively large scale.

While PEDOT has shown considerable potential for these applications, the polymer is relatively hydrophobic, and can show issues with adhesion to solid surfaces. It also does not have any specific functionality for optimizing interactions with living tissue. This leads to issues in long-term performance, due to the possibility of cracking or delamination of the film, and unfavourable interactions with biological media.

Therefore, creating thiophene monomers with functionalized side groups, which can be polymerized to make new polymers and/or copolymers with controlled, variable amounts of a desired chemistry have been investigated. Examples include, but are not limited to an azidomethyl-EDOT that was polymerized and post-functionalized with various alkynes using Cu+ click chemistry; thiol-ene click chemistry to attach a variety of side groups to polythiophenes; and carboxylic acid side groups to attach peptides to surfaces and improve adhesion.

However, there is still a need for novel and cost-effective ways to produce thiophene monomers with biofunctionalized side groups that can be polymerized to make new biofunctional polymers and/or copolymerized.

SUMMARY OF THE INVENTION

Disclosed herein are design, synthesis, and characterization of a number of novel functionalized 3,4 alkylenethiophene monomers, corresponding polymers and copolymers thereof.

Various exemplary aspects of the present invention may be summarized as follows:

In an aspect of the present invention, there is provided a functionalized 3,4-alkylenedioxythiophene (ADOT+) monomer represented by a chemical formula $(CR^1R^2)(CR^3R^4)(CR^5R^6)_xO_2C_4H_2S$ (where A represents $(CR^1R^2)(CR^3R^4)(CR^5R^6)_x$), wherein x=0 or 1. When x=0, the functionalized 3,4-alkylenedioxythiophene monomer is a functionalized 3,4-ethylenedioxythiophene (EDOT+; where E represents $(CR^1R^2)(CR^3R^4)$) and when x=1, the functionalized 3,4-alkylenedioxythiophene monomer is a functionalized 3,4-propylenedioxythiophene (ProDOT+; where Pro represents $(CR^1R^2)(CR^3R^4)(CR^5R^6)$). Each of $R^1$, $R^2$, $R^3$, $R^4$, $R^5$, and $R^6$ is independently selected from hydrogen, a hydrocarbyl moiety, and a heteroatom-containing functional group, such that at least one of $R^1$, $R^2$, $R^3$, $R^4$, $R^5$, and $R^6$ comprises the heteroatom-containing functional group selected from an aldehyde, a maleimide, and their derivatives thereof.

In an embodiment of the functionalized 3,4-alkylenedioxythiophene monomer, the ADOT+ monomer is a derivative of an ADOT-aldehyde or an ADOT-maleimide. The derivative can be obtained by reaction with a hydrocarbyl moiety comprising a second heteroatom functional group selected from thiol, hydroxyl, amines and salts thereof, amides, ketone, nitrile, urea, and carboxylic acid and salts and esters thereof.

In an aspect, at least one of $R^1$, $R^2$, $R^3$, $R^4$, $R^5$, and $R^6$ is an aldehyde group and the functionalized 3,4-alkylenedioxythiophene monomer is an aldehyde derivative represented by a chemical formula $(ADOT-CH_2-NH)_pY$, wherein p=1-2 and Y is a hydrocarbyl moiety. In an embodiment, Y is a biofunctional hydrocarbyl moiety selected from dopamine, L-tyrosine, tyramine, norepinephrine, 3-methoxytyramine, polyethylene glycol, polyethylene glycol amine, and phospholipids.

In another aspect, at least one of $R^1$, $R^2$, $R^3$, $R^4$, $R^5$, and $R^6$ is a maleimide group and the functionalized 3,4-alkylenedioxythiophene monomer is a maleimide derivative represented by a chemical formula $(ADOT-(CH_2)_q-N)_pZ$, and wherein p=1-2; q is 0-10; Z is a hydrocarbyl moiety. In an embodiment, Z is a biofunctional hydrocarbyl moiety selected from adamantane, cholesterol, L-cysteine hydrochloride, L-tyrosine, dopamine, tyramine, norepinephrine, 3-methoxytyramine, polyethylene glycol, polyethylene glycol amine, and phospholipids.

In another aspect, there is provided a biofunctionalized 3,4-alkylenedioxythiophene monomer represented by a chemical formula $(CR^1R^2)(CR^3R^4)(CR^5R^6)_xO_2C_4H_2S$ (A'DOT+, where A' represents $(CR^1R^2)(CR^3R^4)(CR^5R^6)_x$), wherein x=0 or 1. When x=0, the functionalized 3,4-alkylenedioxythiophene monomer is 3,4-ethylenedioxythiophene (E'DOT+; where E' represents $(CR^1R^2)(CR^3R^4)$) and when x=1, the functionalized 3,4-alkylenedioxythiophene monomer is functionalized 3,4-propylenedioxythiophene (Pro'DOT+; where Pro' represents $(CR^1R^2)(CR^3R^4)(CR^5R^6)$). Each of $R^1$, $R^2$, $R^3$, $R^4$, $R^5$, and $R^6$ can be independently selected from hydrogen, a hydrocarbyl group, and a heteroatom-containing functional group, such that at least one of $R^1$, $R^2$, $R^3$, $R^4$, $R^5$, and $R^6$ is replaced by a direct bond to an amide group, an azide group, or an ester group of a biofunctional hydrocarbyl moiety.

In some embodiments, the biofunctionalized 3,4-alkylenedioxythiophene monomer has one of the following structures:

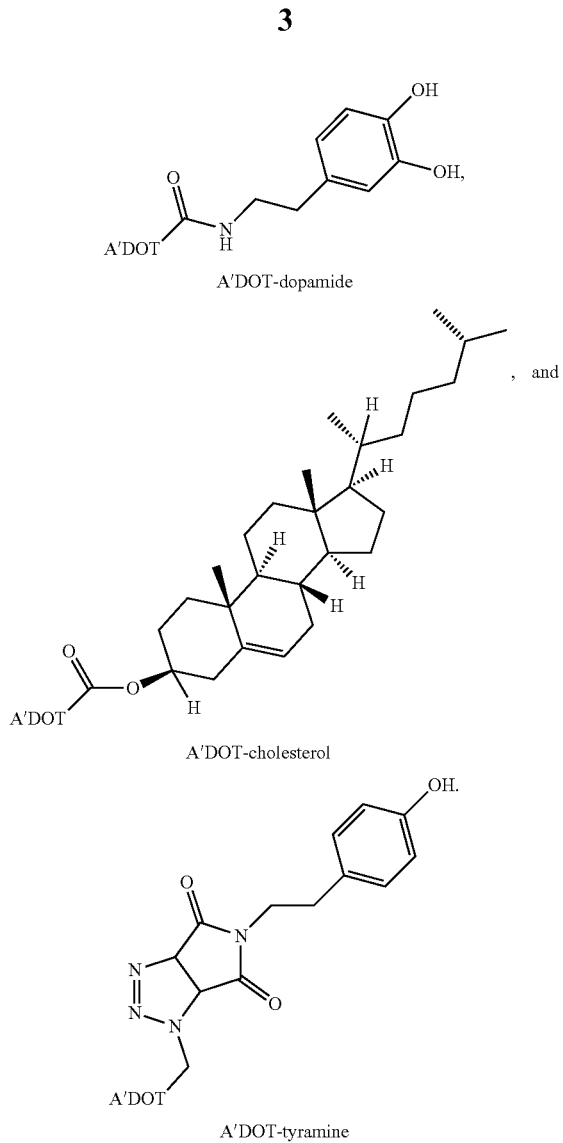

A'DOT-dopamide

A'DOT-cholesterol

A'DOT-tyramine

In another aspect, there is provided a functionalized polymer prepared by polymerization of at least one functionalized or biofunctionalized 3,4-alkylenedioxythiophene monomer, as disclosed hereinabove. The functionalized polymer may be represented by a chemical formula: $[(CR^1R^2)(CR^3R^4)(CR^5R^6)_xO_2C_4S]_m$, where m is a degree of polymerization and is in a range of 2 to 100.

In some embodiments, the functionalized polymer has one of the following general structures:

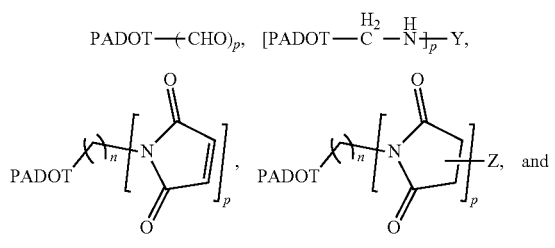

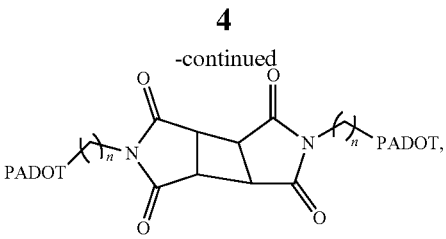

where n=1-10; p=1-2; and wherein each of Y and Z is a of Y and Z is a hydrocarbyl moiety.

In an aspect of the functionalized polymer, the hydrocarbyl moiety is a biofunctional hydrocarbyl moiety selected from adamantane, cholesterol, L-cysteine hydrochloride, L-tyrosine, dopamine, tyramine, norepinephrine, 3-methoxytyramine, polyethylene glycol, polyethylene glycol amine, and phospholipids, and the resulting polymer is a biofunctionalized polymer.

In an embodiment, the functionalized polymer is prepared by copolymerization of at least one functionalized or biofunctionalized monomer, as disclosed hereinabove and at least one additional monomer. Any suitable additional monomers may be used such as 3,4-propylenedioxythiophene (ProDOT) and 3,4-ethylenedioxythiophene (EDOT).

In an aspect, there is provided a method of making a polymer, the method comprising polymerizing at least one functionalized or biofunctionalized monomer, as disclosed hereinabove. Any suitable method of polymerizing may be used such as electropolymerizing.

In another aspect, there is an electronic biomedical device comprising the functionalized polymers as disclosed hereinabove.

DETAILED DESCRIPTION OF THE INVENTION

Figure 1:
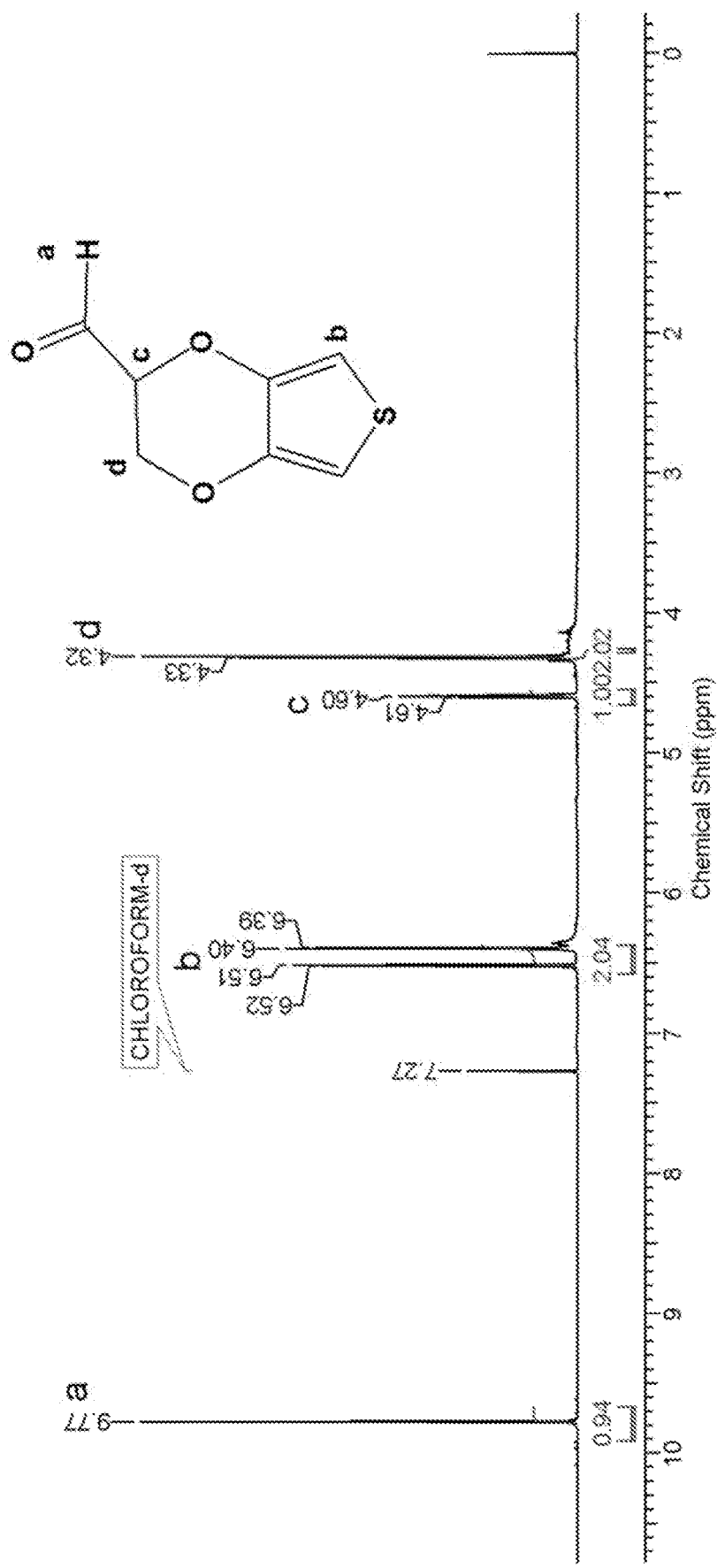
FIG. 1 displays $^1$H-NMR spectrum (in $CDCl_3$) of 2'-Carbaldehyde-3,4-ethylenedioxythiophene (EDOT-aldehyde), according to embodiments of the present invention.

The invention provides a simple and general method for the synthesis of electroactive biofunctional thiophene monomers containing a wide variety of functional and/or hydrocarbyl side chains. Using the methods described herein, a single precursor having an aldehyde or a maleimide or an acid group can be used as a starting point to synthesize a wide range of useful, biofunctional monomers using one-step chemistry.

The ability to create biofunctionalized conjugated polymers is expected to be important for improving interactions with solid substrates, and for tailoring the biological response with living tissue. It may also be possible to create functional, soluble conjugated polymers that could be processed into useful fibers or films. Selecting different substituted monomers for incorporation into a thiophene polymer also permits the phobicity of the polymer to be adjusted as may be desired for a particular end-use application. For example, if the substituent on the monomer is hydrophobic, such as a long chain alkyl group, the resulting polymer derived therefrom will generally be more hydrophobic than a polymer prepared using a monomer bearing a hydrophilic substituent (such as a substituent containing one or more sulfonic acid, polyoxyethylene, hydroxyl, or carboxylic acid functional groups). The solubility of the polymer in various solvents may also be adjusted as may be desired by selection of different substituents/functional groups.

As used herein, the term "functionalized 3,4-alkylenedioxythiophene" is used interchangeably with ADOT+, ADOT-aldehyde, and ADOT-maleimide, and A'DOT+, and their derivatives thereof, as disclosed herein below. Similarly, the term "functionalized 3,4-ethylenedioxythiophene" is used interchangeably with EDOT+, EDOT-aldehyde, EDOT-maleimide, E'DOT+, and their derivatives thereof. The term "functionalized 3,4-propylenedioxythiophene" is used interchangeably with ProDOT+, ProDOT-aldehyde, and ProDOT-maleimide, Pro'DOT+, and their derivatives thereof.

As used herein the term "biofunctional thiophene" monomers is used interchangeably with biofunctional ADOT+ or A'DOT+ monomers and refers to ADOT+ or A'DOT+ monomers (including EDOT+, ProDOT+, E'DOT+, and Pro'DOT+ monomers) comprising a biologically active (bioactive) moiety or a hydrocarbyl moiety having a functionality, which displays reduced negative biological response. As used herein the term "bioactive" moieties refers to materials that has an effect on or are capable of inducing a response from living cells, tissues, or organisms. Exemplary bioactive moieties include, but are not limited to adamantane, cholesterol, L-cysteine hydrochloride, L-tyrosine, dopamine, tyramine, norepinephrine, 3-methoxytyramine, polyethylene glycol, polyethylene glycol amine, phospholipids, and the like.

As used herein, the term "PADOT" refers to poly(3,4-alkylenedioxythiophene) (poly(ADOT)) and is used interchangeably with poly(functionalized 3,4-alkylenedioxythiophene) (PADOT+ and PA'DOT+), PADOT-aldehyde, PADOT-aldehyde-derivative, PADOT-maleimide, and PADOT-maleimide-derivative.

As used herein, the term "biofunctionalized polythiophenes" is used interchangeably with the terms "poly(biofunctionalized 3,4-alkylenedioxythiophene)," "PADOT+," "P'ADOT+," and refers to polymers and copolymers synthesized from at least one biofunctional ADOT+ monomer, biofunctional A'DOT+ monomer, and their derivatives thereof.

In some embodiments, as used herein, the term "biofunctional thiophene" monomers refers to thiophene monomers having a functionality, which displays reduced negative biological response. Often polymers are rejected by biological systems, however, by appropriate choice of functionality in the "biofunctional thiophene" monomers, and thereby in the corresponding biofunctional polymers, it is possible to have biofunctional polymers which displays reduced negative biological response.

In an aspect, there is provided a functionalized 3,4-alkylenedioxythiophene (ADOT+) monomer represented by a chemical formula $(CR^1R^2)(CR^3R^4)(CR^5R^6)_xO_2C_4H_2S$, where A represents $(CR^1R^2)(CR^3R^4)(CR^5R^6)$ and x can be 0 or 1.

In an embodiment, x=0, and the ADOT+ monomer is a functionalized 3,4-ethylenedioxythiophene (EDOT+; where E represents $(CR^1R^2)(CR^3R^4)$), having a structure as shown below. In another embodiment, x=1, and the ADOT+ monomer is a functionalized 3,4-propylenedioxythiophene (ProDOT+; where Pro represents $(CR^1R^2)(CR^3R^4)(CR^5R^6)$), as shown below.

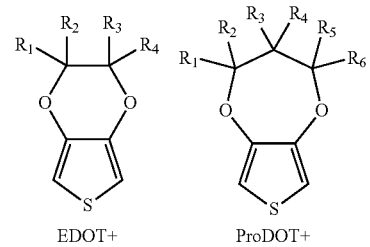

EDOT+      ProDOT+

In an embodiment of the ADOT+ monomer, each of $R^1$, $R^2$, $R^3$, $R^4$, $R^5$, and $R^6$ can be independently selected from hydrogen, a hydrocarbyl moiety, and a heteroatom-containing functional group, such that at least one of $R^1$, $R^2$, $R^3$, $R^4$, $R^5$, and $R^6$ comprises the heteroatom-containing functional group. In an embodiment of the ADOT+ monomer, one of $R^1$, $R^2$, $R^3$, $R^4$, $R^5$, and $R^6$ comprises an aldehyde, a maleimide, or their derivatives thereof.

The hydrocarbyl moiety typically contains from 1 to about 25 carbon atoms, although higher molecular weight monomers are also considered within the scope of the invention. The hydrocarbyl moiety may be completely aliphatic, or completely aromatic, or may contain both aliphatic and aromatic components. Furthermore, the aliphatic portions of the hydrocarbyl moiety may be linear or branched; the moiety may also contain alicyclic components. Preferably, any aliphatic portions of the hydrocarbyl moiety are saturated.

In an embodiment, the hydrocarbyl moiety is a biofunctional hydrocarbyl moiety. Suitable examples of biofunctional hydrocarbyl moieties include, but are not limited to adamantane, cholesterol, L-cysteine hydrochloride, L-tyrosine, dopamine, tyramine, norepinephrine, 3-methoxytyramine, polyethylene glycol, polyethylene glycol amine, phospholipids, and the like.

Any suitable heteroatom-containing functional group may be used, including, but not limited to, aldehydes and their derivatives thereof, maleimides and their derivatives thereof, amines and salts thereof, amides, azides, silanes, ether, sulfonic acid and salts and esters thereof, thiol, hydroxyl, and carboxylic acid and salts and esters thereof.

In an embodiment, when x=0 and the ADOT+ monomer is an EDOT+ monomer, $R_1$, $R_2$, $R_3$ and $R_4$ groups can be located in a cis configuration or a trans configuration to each other. In an embodiment, the EDOT+ monomer is a mixture of trans/cis configurations. In yet another embodiment, $R_1$ and $R_2$ are the same groups and $R_3$ and $R_4$ are different groups, and the resulting EDOT+ monomer shows chirality in R or S configurations or is a mixture of R and S configuration.

Any suitable method may be used to prepare ADOT+ monomers as disclosed hereinabove. In an embodiment, ADOT-aldehyde can be prepared by reacting hydroxymethyl-3,4-alkylenedioxythiophene (ADOT-OH) with Dess-Martin periodinane in a suitable solvent.

In an exemplary embodiment, the ADOT+ monomer is an ADOT-maleimide (ADOT-MA). The ADOT-maleimide can be prepared by reacting 3,4-dimethoxythiophene and chloroalkanediol in the presence of a catalytic amount of p-toluenesulfonic acid (p-TSA) to obtain chloro-methyl-3,4-alkylenedioxythiophene (ADOT-Cl). The ADOT-Cl can then be reacted with sodium azide in a suitable solvent to substitute the chloro group and to thereby obtain azidomethyl-3,4-alkylenedioxythiophene (ADOT-$N_3$). The ADOT-$N_3$ can then be reduced using triphenyl phosphine and sodium hydroxide to obtain aminomethyl-3,4-alkylenedioxythiophene (ADOT-$NH_2$). The ADOT-$NH_2$ can be further reacted with maleic anhydride in a solvent to obtain maleimideomethyl-3,4-alkylenedioxythiophene (ADOT-MA). An exemplary method of making EDOT-MA is disclosed hereinbelow in Scheme 6 in Example 3.

Derivatives of ADOT+

In an aspect, the ADOT+ monomer, as disclosed hereinabove is a derivative of an ADOT-aldehyde or an ADOT-maleimide and can be obtained by one step reaction with a compound comprising a second heteroatom functional group selected from thiol, hydroxyl, amines and salts thereof, amides, ketone, nitrile, urea, and carboxylic acid and salts and esters thereof.

In an embodiment of the ADOT+ monomer as disclosed hereinabove, at least one of the $R^1$, $R^2$, $R^3$, $R^4$, $R^5$, and $R^6$ is an aldehyde group, and thereby the resulting ADOT+ monomer is an ADOT-CHO. In another embodiment, the ADOT-CHO is reacted with one or more primary amine compounds (Y—$NH_2$) to form imine derivatives, also known as Schiff bases (compounds having a C=N function, which are formed insitu as intermediates). Subsequently, imine derivatives can be reduced by sodium borohydride to obtain ADOT-imides. In an embodiment, imide derivatives of ADOT-aldehyde may be represented by a chemical formula (ADOT-$CH_2$—NH)$_p$Y, where p=1-2 and Y is any hydrocarbyl moiety, including, but not limited to dopamine, L-tyrosine, tyramine, norepinephrine, 3-methoxytyramine, polyethylene glycol, polyethylene glycol amine, and phospholipids.

Scheme 1 below shows exemplary amine derivatives of EDOT-aldehyde:

Scheme 1

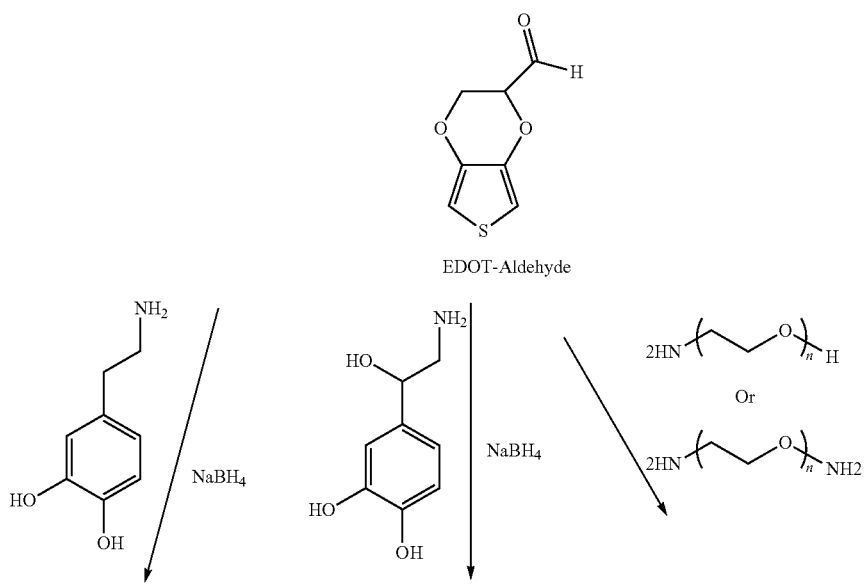

EDOT-Aldehyde

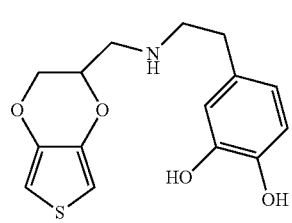
1
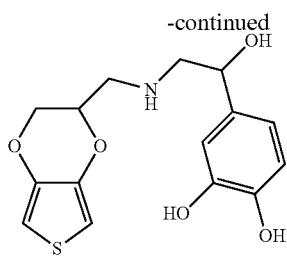
2
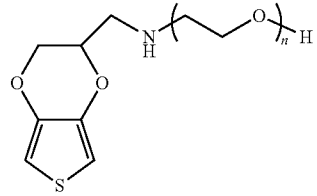
3
Or
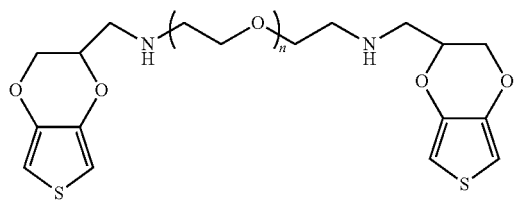
4
Scheme 2 below shows exemplary amine derivatives of ProDOT-aldehyde:
Scheme 2
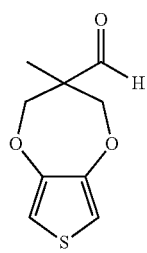
ProDOT-Aldehyde
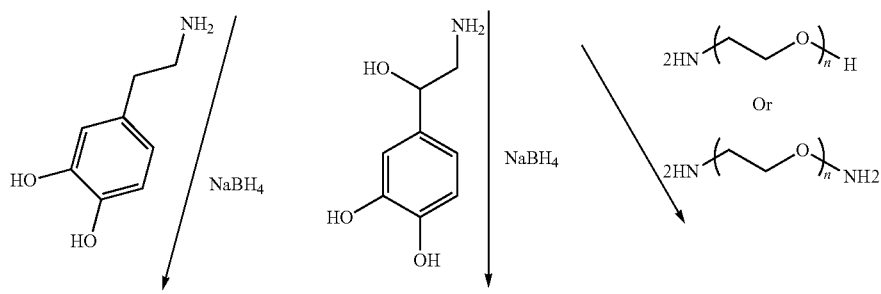

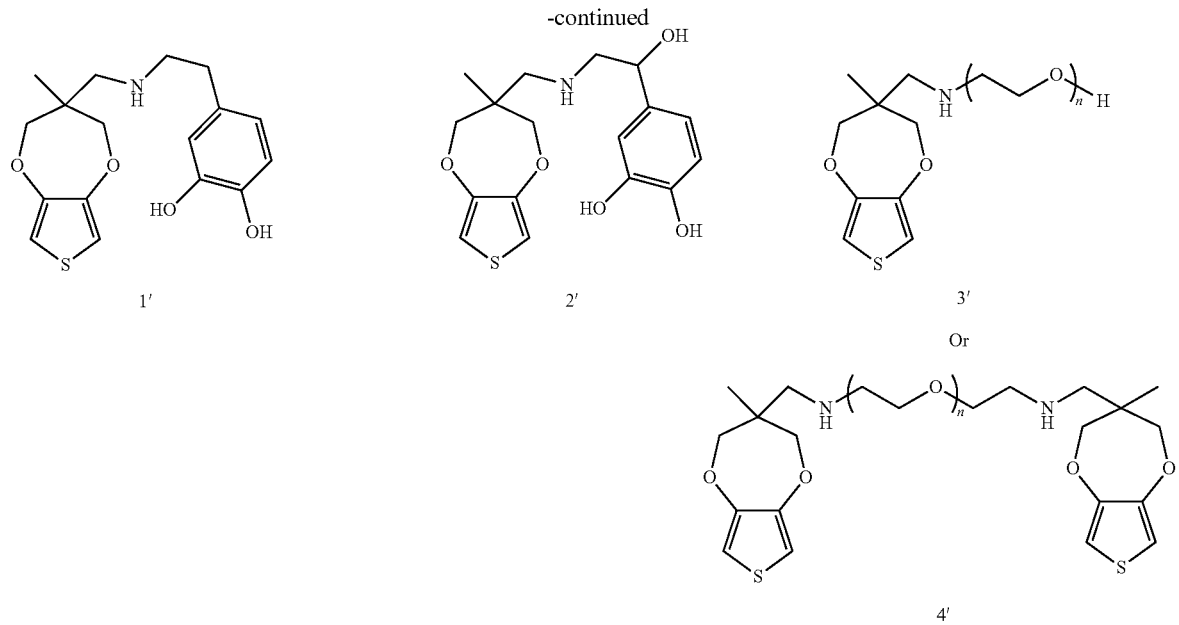

1'       2'       3'

Or

4'

In another embodiment of the ADOT+ monomers, as disclosed hereinabove, at least one of the $R^1$, $R^2$, $R^3$, $R^4$, $R^5$, and $R^6$ is a maleimide group, and the resulting the ADOT+ monomer is an ADOT-MA. The maleimide functionality of the ADOT-MA can undergo a variety of different chemical reactions including Michael addition, Diels-Alder reactions, cycloaddition, free radical polymerization, as well as photo- and thermally-induced cross-linking to yield a wide range of derivatives of ADOT-MA.

In an embodiment of the ADOT+ monomer, at least one of $R^1$, $R^2$, $R^3$, $R^4$, $R^5$, and $R^6$ is a maleimide group and the ADOT+ monomer is a maleimide derivative represented by a chemical formula (ADOT-$(CH_2)_q$—N$)_p$Z, where p=1-2; q is 0-10; Z is any suitable hydrocarbyl group as disclosed hereinabove. The maleimide derivatives can be obtained by reacting ADOT-MA with a suitable compound having an amine, an azide, a thiol, or a furan as a reactive second heteroatom containing functional group.

Z can be any suitable hydrocarbyl moiety, as disclosed hereinabove. In an embodiment, Z is a suitable a biofunctional hydrocarbyl moiety selected from adamantane, cholesterol, L-cysteine hydrochloride, L-tyrosine, dopamine, tyramine, norepinephrine, 3-methoxytyramine, polyethylene glycol, polyethylene glycol amine, phospholipids, and the like.

Suitable examples of the derivatives of ADOT-MA, include, but are not limited to, ADOT-MA_adamantane, ADOT-MA_cholesterol, ADOT-MA_cysteine hydrochloride, ADOT-MA_polyethylene glycol, ADOT-MA_phospholipids, and ADOT-MA_dopamine.

Exemplary reactions of ADOT-MA to form derivatives of ADOT-MA are shown below in Scheme 3:

Sheme 3

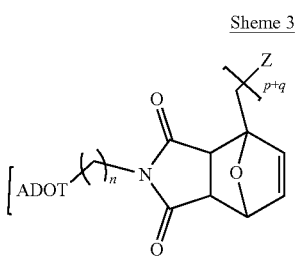

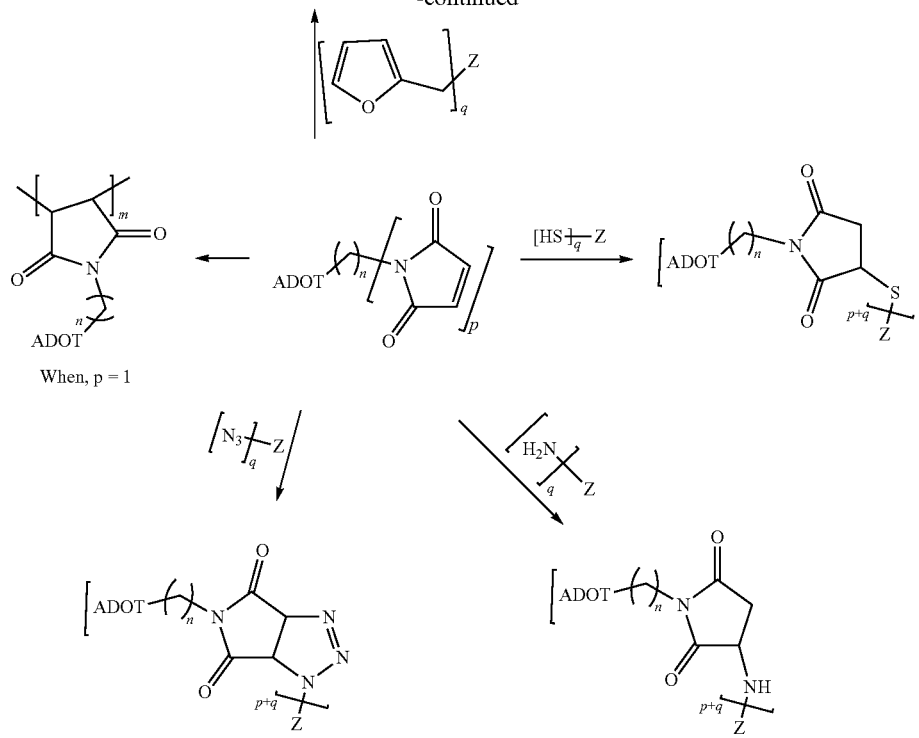

A'DOT+ Monomers

In another aspect, there is provided a biofunctionalized 3,4-alkylenedioxythiophene (A'DOT+) monomer represented by a chemical formula $(CR^1R^2)(CR^3R^4)(CR^4R^6)_xO_2C_4H_2S$ (where A' represents $(CR^1R^2)(CR^3R^4)(CR^4R^6)_x)$, wherein each of $R^1, R^2, R^3, R^4, R^5$, and $R^6$ is independently selected from hydrogen, a hydrocarbyl group, and a heteroatom-containing functional group, and wherein one of $R^1, R^2, R^3, R^4, R^5$, and $R^6$ group is replaced by a direct bond to an amide group, an azide group, or an ester group of a biofunctional moiety.

In embodiments of A'DOT+ monomer, x can be 0 or 1. When x=0, the A'DOT monomer is E'DOT+ monomer and when x=1, the A'DOT+ monomer is Pro'DOT monomer.

Suitable examples of biofunctional A'DOT+ monomers include, but are not limited to:

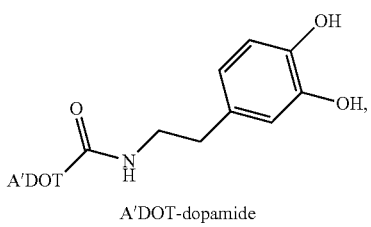

A'DOT-dopamide

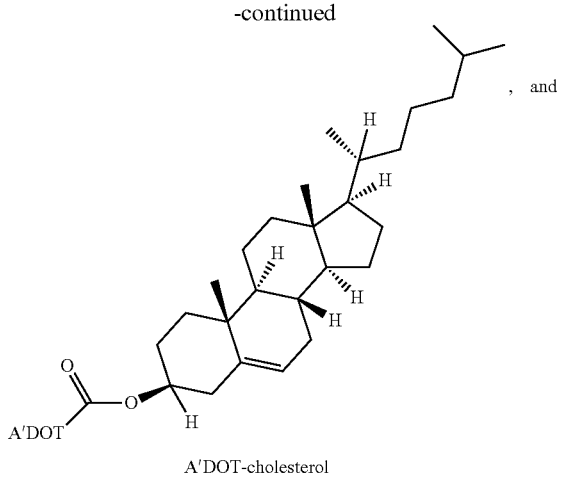

, and

A'DOT-cholesterol

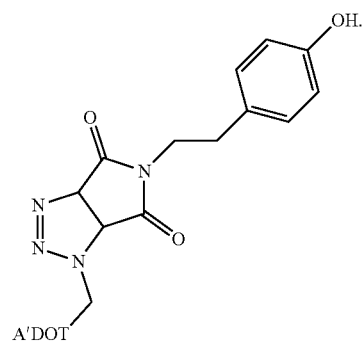

A'DOT-tyramine

Polymers of ADOT+ and/or A'DOT+ Monomers

In another aspect of the present invention, there is provided a process for preparing a polymer containing one or more units derived from the ADOT+ and/or A'DOT+ monomers, as disclosed hereinabove. The resulting polymer may be represented by a chemical formula: $[(CR^1R^2)(CR^3R^4)(CR^5R^6)_xO_2C_4S]_m$ where m is a degree of polymerization and is in a range of 2 to 100, and where each one of $R^1$, $R^2$, $R^3$, $R^4$, $R^5$, and $R^6$ is independently selected from H, a hydrocarbyl moiety, and a heteroatom-containing functional group, such that such that at least one of $R^1$, $R^2$, $R^3$, $R^4$, $R^5$, and $R^6$ comprises the heteroatom-containing functional group. In an embodiment one of $R^1$, $R^2$, $R^3$, $R^4$, $R^5$, and $R^6$ comprises an aldehyde, a maleimide, or their derivatives thereof. In another embodiment, one of $R^1$, $R^2$, $R^3$, $R^4$, $R^5$, and $R^6$ is replaced by a direct bond to an amide group, an azide group, or an ester group.

Hence, the resulting polymer, as shown below, may contain substituents (optionally including functional groups) derived from the ADOT+ monomer or the A'DOT+ monomer, which are pendant to a polythiophene backbone.

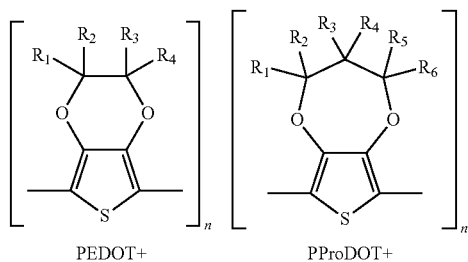

PEDOT+   PProDOT+

Suitable examples of poly(functionalized 3,4-alkylenedioxythiophene) include, but are not limited to:

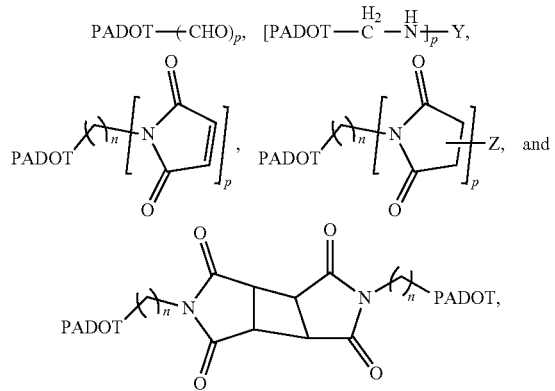

where n=1-10; p=1-2.

In an embodiment, each of Y and Z is a hydrocarbyl moiety, as disclosed hereinabove. In an embodiment, each of Y and Z is a biofunctional hydrocarbyl moiety, as disclosed hereinabove.

In another embodiment, the ADOT+ monomer comprises a biofunctional hydrocarbyl moiety and the resulting polymer and/or copolymer, formed from the biofunctional ADOT+ monomer comprising the biofunctional monomer, is a biofunctional polythiophene.

According to an embodiment of the present invention, the polymerization process is a chemical or an electrochemical process. Homopolymers as well as copolymers may be prepared. For example, ADOT+ monomer or A'DOT+ monomer in accordance with the invention may be homopolymerized. Mixtures of two or more different ADOT+ and/or A'DOT+ monomers in accordance with the invention may be copolymerized. The present invention also includes the copolymerization of one or more ADOT+ and/or A'DOT+ monomers as disclosed hereinabove with one or more other types of monomers, such as other thiophenes such as ProDOT, EDOT or ProDOT-ene or non-thiophene comonomers such as pyrroles. The relative proportions of ADOT+ monomer, A'DOT+ monomer and other types of monomers may be selected in accordance with the degree of substitution and/or functionalization contributed by the ADOT+ monomer or A'DOT+ monomer which is desired in the polymer. In an embodiment, the polymer is prepared by copolymerization of at least one ADOT+ monomer or A'DOT+ monomer and at least one additional monomer including at least one of 3,4-propylenedioxythiophene (ProDOT), 3,4-ethylenedioxythiophene (EDOT), or 3-allyl-3,4-dihydro-2H-thieno[3,4-b][1,4]dioxepine Chemical Polymerization Chemical polymerization, according to the present invention, can be carried out oxidatively or reductively. The oxidation agents used for the oxidative polymerization of pyrrole, such as described for example in Journal of the American Chemical Society, volume 85, pages 454-458 (1963) and J. Polymer Science Part A Polymer Chemistry, volume 26, pages 1287-1294 (1988), can be utilized for the oxidative polymerization of thiophenes and may be adapted for use with the monomers and crosslinkers of the present invention.

According to one embodiment of the polymerization process according to the present invention, the process is a chemical process in which inexpensive and easily accessible oxidizing agents such as iron(III) salts such as $FeCl_3$ (ferric chloride), the iron(III) salts of organic acids, e.g. $Fe(OTs)_3$, $H_2O_2$, $K_2Cr_2O_7$, alkali and ammonium persulphates, copper perchlorate, iron perchlorate, alkali perborates and potassium permanganate are used therein to initiate the polymerization.

Theoretically, the oxidative polymerization of thiophenes requires 2.25 equivalents of oxidizing agent per mole of thiophene [see e.g. J. Polymer Science Part A Polymer Chemistry, volume 26, pages 1287-1294 (1988)]. In practice, an excess of 0.1 to 2 equivalents of oxidation agent is typically used per polymerizable unit. The use of persulphates and iron(III) salts has the great technical advantage that they do not act corrosively. Oxidative polymerization can be accelerated by heating the monomer(s), for example, after placing a coating of the monomer(s) on a substrate surface.

Reductive polymerization can be performed using any of the conventional reductive polymerization techniques known in the thiophene art, such as the Stille (organotin) or Suzuki (organoboron) routes or with nickel complexes.

Electrochemical Polymerization

ADOT+ and A'DOT+ monomers, as disclosed hereinabove also can be polymerized electrochemically. Electrochemical oxidative polymerization of such monomers may be carried out at any temperature effective to permit the polymerization to proceed at a practicably rapid rate. Typically, temperatures between about −20° C. and 60° C. are suitable. The reaction time, depending upon the particular monomer or mixture of monomers, is generally between a few seconds and several hours. Electrochemical polymerization of thiophene compounds was described in 1994 by Dietrich et al. in Journal Electroanalytical Chemistry, volume 369, pages 87-92. In a typical electrochemical polymerization, a potential is applied across a solution containing a thiophene-type monomer and an electrolyte, producing a polymeric film on the anode. Oxidation of the monomer produces a radical cation, which can then couple with a second radical cation to form a dication dimer, or with another monomer to produce a radical cation dimer. Growth of the polymer chain takes place by a series of such coupling reactions.

Inert liquids suitable for use during electrochemical oxidation and polymerization of the monomers and crosslinkers of the present invention include, but are not limited to: water, alcohols such as methanol and ethanol, ketones such as acetophenone, halogenated hydrocarbons such as methylene chloride, chloroform, tetrachloromethane and fluorohydrocarbons, esters such as ethyl acetate and butyl acetate, aromatic hydrocarbons such as benzene, toluene and xylene, aliphatic hydrocarbons such as pentane, hexane, heptane and cyclohexane, nitriles such as acetonitrile and benzonitrile, sulfoxides such as dimethylsulfoxide, sulfones such as dimethylsulfone, phenylmethylsulfone and sulfolan, liquid aliphatic amides such as methyl acetamide, dimethyl acetamide, dimethyl formamide, pyrrolidone, N-methylpyrrolidone, caprolactam, N-methyl-caprolactam, aliphatic and mixed aliphatic and aromatic ethers such as diethylether and anisole, liquid ureas such as tetramethylurea or N,N-dimethyl-imidazolidinone.

Electrolyte additives for use in the electrochemical polymerization of the ADOT+ and/or A'DOT+ monomers of the invention are preferably free acids or the usual conducting salts, which exhibit a certain solubility in the solvent used. Particularly suitable electrolytes are alkali, alkaline earth or optionally alkylated ammonium, phosphonium, sulfonium or oxonium cations in combination with perchlorate, tosylate, tetrafluoroborate or hexafluorophosphonate anions. The electrolyte additives may be used in such quantities that a current of at least 0.1 mA flows during electrochemical oxidation.

Electrochemical polymerization can be carried out continuously or discontinuously. Known electrode materials are ITO-covered glass, precious metal or steel mesh, carbon-filled polymers, evaporated metal-coated insulator layers and carbon felt.

Current densities during electrochemical oxidation may vary within wide limits. According to one embodiment of the present invention, the current density is 0.0001 to 100 mA/cm$^2$. According to another embodiment of the process according to the present invention, the current density is 0.01 to 40 mA/cm$^2$. At such current densities, voltages of ca. 0.1 to 50 V are typically set up.

Chemically or electrochemically prepared polymers derived from the ADOT+ and/or A'DOT+ monomers in accordance with the invention exhibit high electrical conductivity together with low absorption of visible light and high absorption to infrared radiation. Therefore layers thereof are highly electrically conducting, highly transparent to visible light and heat shielding. Such polymers can be applied by a wide variety of techniques including printing techniques in which the polymer is applied, for example, as an ink or paste using standard techniques, the properties of the paste or ink being adapted to the particular printing technique by adding one of more of organic solvents, binders, surfactants and humectants, to a wide variety of rigid and flexible substrates, e.g. ceramics, glass and plastics, and are particularly suitable for flexible substrates such as plastic sheeting and the substrates can be substantially bent and deformed without the polythiophene layer losing its electrical conductivity. Such polymers especially lend themselves to the production of electroconductive patterns.

The functionalized 3,4-alkylenedioxythiophene-based polymers of the present invention can therefore be utilized, for example, in electrochromic devices, photovoltaic devices, batteries, diodes, capacitors and organic and inorganic electroluminescent devices, in electromagnetic shielding layers, in heat shielding layers, in antistatic coatings for a wide variety of products including photographic film, thermographic recording materials and photothermographic recording materials, in smart windows, in sensors for organic and bio-organic materials (e.g., chemical sensors), in field effect transistors, in printing plates, in conductive resin adhesives, in solar cells, in photochemical resists, in nonlinear optic devices and in free-standing electrically conductive films.

Applications for polymers in accordance with the invention include both static applications, which rely upon the intrinsic conductivity of the polymer combined with its ease of processing and material properties as a polymeric material, and dynamic applications, which utilize changes in the conductive and/or optical properties of the polymer resulting either from application of electric potentials or from environmental stimuli.

Polymers in accordance with the invention may be doped, in order to modify their conductivity and other properties. Suitable dopants may include, for example, halogens such as iodine and bromine, organic acids such as trifluoroacetic acid, propionic acid, and sulfonic acids, ferric chloride, and the like.

In an aspect, there is provided an electronic biomedical device comprising the biofunctional polythiophenes, as disclosed hereinabove. Suitable electronic biomedical devices include, but are not limited to, pacemakers, cochlear implants, and the like.

Aspects of the Invention

Certain illustrative, non-limiting aspects of the invention may be summarized as follows:

Aspect 1. A functionalized 3,4-alkylenedioxythiophene (ADOT+) monomer represented by a chemical formula $(CR^1R^2)(CR^3R^4)(CR^5R^6)_x O_2 C_4 H_2 S$ (where A represents $(CR^1R^2)(CR^3R^4)(CR^5R^6)_x$), wherein x=0 or 1, when x=0, the functionalized 3,4-alkylenedioxythiophene monomer is a functionalized 3,4-ethylenedioxythiophene (EDOT+; where E represents $(CR^1R^2)(CR^3R^4)$) and when x=1, the functionalized 3,4-alkylenedioxythiophene monomer is a functionalized 3,4-propylenedioxythiophene (ProDOT+; where Pro represents $(CR^1R^2)(CR^3R^4)(CR^5R^6)$;

wherein each of $R^1$, $R^2$, $R^3$, $R^4$, $R^5$, and $R^6$ is Independently selected from hydrogen, a hydrocarbyl moiety, and a heteroatom-containing functional group; and wherein at least one of $R^1$, $R^2$, $R^3$, $R^4$, $R^5$, and $R^6$ comprises the heteroatom-containing functional group selected from an aldehyde, a maleimide, and their derivatives thereof.

Aspect 2. The functionalized 3,4-alkylenedioxythiophene monomer in accordance with Aspect 1, wherein the ADOT+ monomer is a derivative of an ADOT-aldehyde or an ADOT-maleimide.

Aspect 3. The functionalized 3,4-alkylenedioxythiophene monomer in accordance with Aspect 2, wherein the derivative is obtained by reaction with a hydrocarbyl moiety comprising a second heteroatom functional group selected from thiol, hydroxyl, amines and salts thereof, amides, ketone, nitrile, urea, and carboxylic acid and salts and esters thereof.

Aspect 4. The functionalized 3,4-alkylenedioxythiophene monomer in accordance with to Aspect 1, wherein at least one of $R^1$, $R_2$, $R^3$, $R^4$, $R^5$, and $R^6$ is an aldehyde group and the functionalized 3,4-alkylenedioxythiophene monomer is an aldehyde derivative represented by a chemical formula $(ADOT\text{-}CH_2\text{--}NH)_pY$, wherein p=1-2 and Y is a hydrocarbyl moiety.

Aspect 5. The functionalized 3,4-alkylenedioxythiophene monomer in accordance with Aspect 4, wherein Y is a biofunctional hydrocarbyl moiety selected from dopamine, L-tyrosine, tyramine, norepinephrine, 3-methoxytyramine, polyethylene glycol, polyethylene glycol amine, and phospholipids.

Aspect 6. The functionalized 3,4-alkylenedioxythiophene monomer in accordance with Aspect 1, wherein at least one of $R^1$, $R^2$, $R^3$, $R^4$, $R^5$, and $R^6$ is a maleimide group and the functionalized 3,4-alkylenedioxythiophene monomer is a maleimide derivative represented by a chemical formula $(ADOT\text{-}(CH_2)_q\text{--}N)_pZ$, and wherein p=1-2; q is 0-10; Z is a hydrocarbyl moiety.

Aspect 7. The functionalized 3,4-alkylenedioxythiophene monomer in accordance with Aspect 6, wherein Z is a biofunctional hydrocarbyl moiety selected from adamantane, cholesterol, L-cysteine hydrochloride, L-tyrosine, dopamine, tyramine, norepinephrine, 3-methoxytyramine, polyethylene glycol, polyethylene glycol amine, and phospholipids.

Aspect 8. A biofunctionalized 3,4-alkylenedioxythiophene monomer represented by a chemical formula $(CR^1R^2)(CR^3R^4)(CR^4R^6)_xO_2C_4H_2S$ (A'DOT+, where A' represents $(CR^1R^2)(CR^3R^4)(CR^5R^6)_x$)

wherein x=0 or 1, when x=0, the functionalized 3,4-alkylenedioxythiophene monomer is 3,4-ethylenedioxythiophene (E'DOT+; where E' represents $(CR^1R^2)(CR^3R^4)$) and when x=1, the functionalized 3,4-alkylenedioxythiophene monomer is functionalized 3,4-propylenedioxythiophene (Pro'DOT+; where Pro' represents $(CR^1R^2)(CR^3R^4)(CR^5R^6)$), wherein each of $R^1$, $R^2$, $R^3$, $R^4$, $R^5$, and $R^6$ is independently selected from hydrogen, a hydrocarbyl group, and a heteroatom-containing functional group, and wherein one of $R^1$, $R^2$, $R^3$, $R^4$, $R^5$, and $R^6$ is replaced by a direct bond to an amide group, an azide group, or an ester group of a biofunctional hydrocarbyl moiety.

Aspect 9. The biofunctionalized 3,4-alkylenedioxythiophene monomer according to Aspect 8 having one of the following structures:

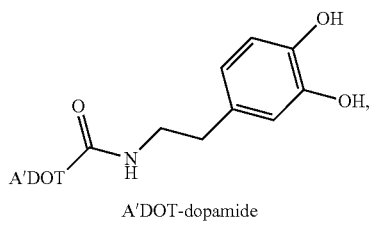

A'DOT-dopamide

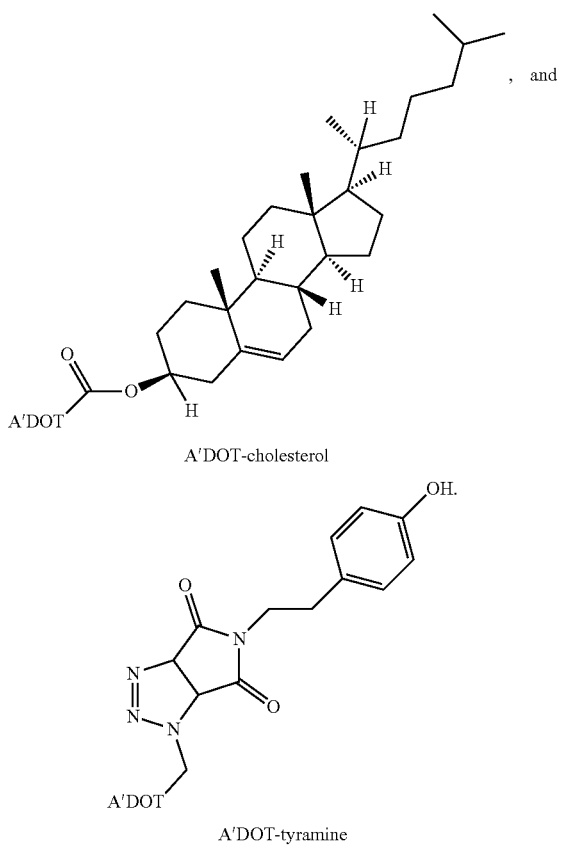

A'DOT-cholesterol

A'DOT-tyramine

Aspect 10. A functionalized polymer prepared by polymerization of at least one monomer in accordance with any one of the Aspects 1-8, wherein the functionalized polymer is represented by a chemical formula: $[(CR^1R^2)(CR^3R^4)(CR^5R^6)_xO_2C_4S]_m$, where m is a degree of polymerization and is in a range of 2 to 100.

Aspect 11. The functionalized polymer in accordance with Aspect 10 having one of the following general structures:

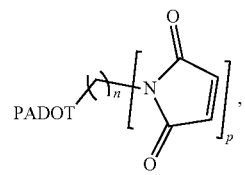

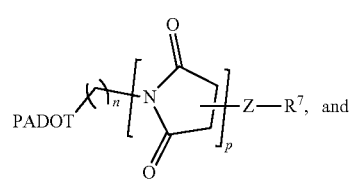

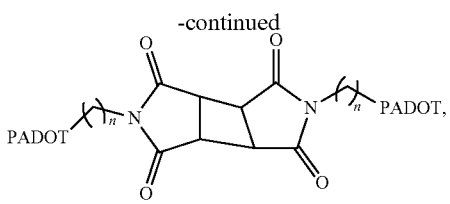

where n=1-10; p=1-2;
wherein each of Y and Z is a of Y and Z is a hydrocarbyl moiety.

Aspect 12. The functionalized polymer in accordance with Aspect 11, wherein the hydrocarbyl moiety is a biofunctional hydrocarbyl moiety selected from adamantane, cholesterol, L-cysteine hydrochloride, L-tyrosine, dopamine, tyramine, norepinephrine, 3-methoxytyramine, polyethylene glycol, polyethylene glycol amine, and phospholipids.

Aspect 13. The functionalized polymer in accordance with Aspect 10, wherein the polymer is prepared by copolymerization of at least one monomer in accordance with any one of the Aspects 1-9 and at least one additional monomer.

Aspect 14. The functionalized polymer in accordance with Aspect 13, wherein the additional monomer includes at least one of 3,4-propylenedioxythiophene (ProDOT) and 3,4-ethylenedioxythiophene (EDOT).

Aspect 15. A method of making a polymer, the method comprising polymerizing at least one monomer in accordance with any one of the Aspects 1-9.

Aspect 16. The method in accordance with Aspect 12, wherein the step of polymerizing comprises electropolymerizing.

Aspect 17. An electronic biomedical device comprising the polymer according to any one of the Aspects 10-14.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel thioephene monomers and polymers and copolymers thereof and methods of making and using thereof. Additionally, in some embodiments, the invention can be construed as excluding any element or process step not specified herein.

EXAMPLES

Examples of the present invention will now be described. The technical scope of the present invention is not limited to the examples described below.

Materials

Materials and their source are listed below:

Hydroxymethyl EDOT (EDOT-OH), Dess-Martin periodinane, maleic anhydride, glacial acetic acid, 1-[Bis(dimethylamino)methylene]-1H-1,2,3-triazolo[4,5-b]pyridinium 3-oxide hexafluorophosphate (HATU), Diisopropylethylamine (DIPEA) 3,4-dihydroxyphenethylamine (Dopamine), cholesterol, 4-(Dimethylamino)pyridine (DMAP), lithium perchlorate ($LiClO_4$), propylene carbonate (PPC), and N-(3-Dimethylaminopropyl)-N'-ethylcarbodiimide hydrochloride (EDCI) were purchased from Sigma Aldrich Chemicals, USA and were used as received. EDOT-COOH was purchased from China. ProDOT-OH, $EDOT-NH_2$, $EDOT-N_3$ and Tyramine-Maleimide were synthesized according to literature procedures. Sodium thiosulfate, sodium sulfate, sodium hydroxide and hydrochloric acid were procured form fisher scientific and were used as received. N,N-Dimethylformamide (DMF), tetrahydrofuran (THF), toluene, chloroform, dichloromethane, ethyl acetate and petroleumether were procured from Fisher Scientific.

Measurement Methods

NMR spectra were recorded on a Bruker 400 MHz spectrometer, at resonance frequencies of 400 MHz for $^1H$ NMR and 100 MHz for $^{13}C$ NMR measurements using $CDCl_3$ and Acetone-$d_6$ as a solvents.

Attenuated total reflectance FTIR (ATR-FTIR) spectra of thiophene monomers were recorded on a PerkinElmer Spectrum 100 ATR-FTIR spectrometer.

UV-Vis spectra of thiophene polymers were recorded on a Shimadzu UV-3600.

Electrochemical polymerization carried out using a Metrohm Autolab PGSTAT128N.

Scanning electron microscopy (SEM) micrographs of thiophene polymers were taken on a JSM-7400F (FE-SEM).

Methods

Example No. 1

Synthesis of 2'-Carbaldehyde-3,4-ethylenedioxythiophene (EDOT-aldehyde)

EDOT-aldehyde was synthesized starting from commercially available EDOT-OH by the route illustrated below in Scheme 4.

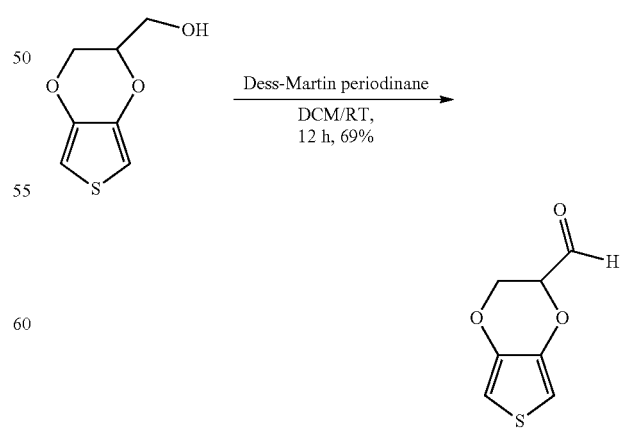

Into a 50 mL two necked round-bottom flask fitted with a magnetic stirring bar were added Dess-Martin periodinane (0.443 g, 1.05 mmol) and dry dichloromethane (20 mL). EDOT-OH (0.150 g, 0.871 mmol) was added to the reaction mixture and stirred at room temperature for 12 h, while consumption of starting material was monitored by TLC. After the reaction was complete, 1M sodium thiosulfate (20 mL) was added. After stirring for 15 minutes, the phases were separated and the aqueous phase was extracted with dichloromethane (2×20 mL). The dichloromethane solution was washed with saturated brine solution (2×20 mL) and dried over anhydrous sodium sulfate, filtered and evaporated under reduced pressure. The crude product was purified by column chromatography using petroleum ether: ethyl acetate (80:20, v/v) as an eluent to afford EDOT-aldehyde (0.102 g, 69%).

EDOT-aldehyde was characterized by FT-IR, $^1$H NMR and $^{13}$C NMR spectroscopy. $^1$H NMR spectrum of the as-synthesized EDOT-aldehyde, as shown in FIG. 1, revealed a signal at 9.77 δ ppm corresponding to aldehyde carbonyl.

$^1$H NMR (400 MHz, CDCl$_3$): δ=9.77 (s, 1H), 6.52 (d, 1H), 6.40 (d, 1H), 4.60 (t, 1H), 4.32 (t, 2H), $^{13}$C NMR: δ=198.4, 141.2, 139.9, 100.9, 77.6, 63.7 ppm.

Example No. 2

Synthesis of 3-methyl-3,4-dihydro-2H-thieno[3,4-b][1,4]dioxepine-3-carbaldehyde (ProDOT-aldehyde)

Scheme 5 represents the route followed for the synthesis of ProDOT-aldehyde starting from ProDOT-OH via one-step reaction pathway. ProDOT-OH was synthesized by the reported procedure (Kim et al. "A Single-Step Synthesis of Electroactive Mesoporous ProDOT-Silica Structures." *Angewandte Chemie International Edition* 54 (29): 8407-10). ProDOT-OH was reacted with Des-Martin periodinane in dry dichloromethane as a solvent at room temperature to obtain ProDOT-aldehyde.

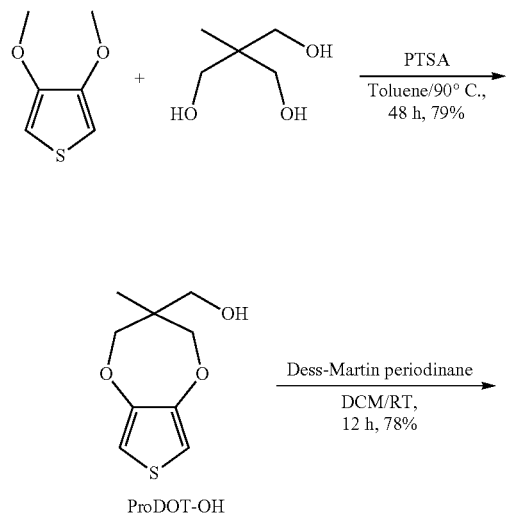

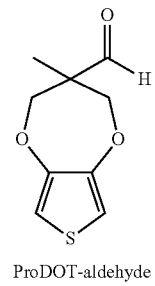

ProDOT-aldehyde

Step 2A: Synthesis of (3-methyl-3,4-dihydro-2H-thieno[3,4-b][1,4]dioxepin-3-yl)methanol (ProDOT-OH)

Into a 500 mL two necked round-bottom flask equipped with a reflux condenser and argon inlet were placed, 3,4-dimethoxythiophene (12.0 g, 83.22 mmol), anhydrous toluene (300 mL) with 1,1,1-tris(hydroxymethyl)ethane (13.0 g, 108.19 mmol) and p-toluenesulfonic acid (p-TSA) (1.43 g, 8.32 mmol). The reaction mixture was stirred at 110° C. for 48 h. The final solution was cooled at room temperature and then the toluene was evaporated under reduced pressure. The solution of 10% sodium bicarbonate (150 mL) was added to the crude and the product was extracted with dichloromethane (3×100 mL). The organic phases were combined, washed with water (2×100 mL) and dried over anhydrous sodium sulfate, filtered and evaporated under reduced pressure. The crude product was purified by column chromatography using petroleumether: dichloromethane (80:20, v/v) as an eluent to afford ProDOT-OH (12.9 g, 79%).

$^1$H NMR (400 MHz, CDCl$_3$): δ=6.51 (s, 2H), 4.09 (s, 2H), 3.79 (d, 2H), 1.85 (s, 1H), 0.95 (s, 3H), $^{13}$C NMR: δ=149.6, 105.7, 76.3, 65.9, 43.8, 16.9 ppm.

Step 2B: Synthesis of 3-methyl-3,4-dihydro-2H-thieno[3,4-b][1,4]dioxepine-3-carbaldehyde (ProDOT-aldehyde)

Into a 50 mL two necked round-bottom flask fitted with a magnetic stirring bar were added Dess-Martin periodinane (0.508 g, 1.20 mmol) and dry dichloromethane (20 mL). ProDOT-OH (0.200 g, 0.998 mmol) was added in the reaction mixture and stirred at room temperature for 12 h, while consumption of starting material was monitored by TLC. After the reaction was complete, 1M sodium thiosulfate (20 mL) was added. After stirring for 15 minutes, the phases were separated and the aqueous phase was extracted with dichloromethane (2×20 mL). The dichloromethane solution was washed with saturated brine solution (2×20 mL) and dried over anhydrous sodium sulfate, filtered and evaporated under reduced pressure. The crude product was purified by column chromatography using petroleum ether: ethyl acetate (80:20, v/v) as an eluent to afford ProDOT-Aldehyde (0.154 g, 78%).

Figure 2:
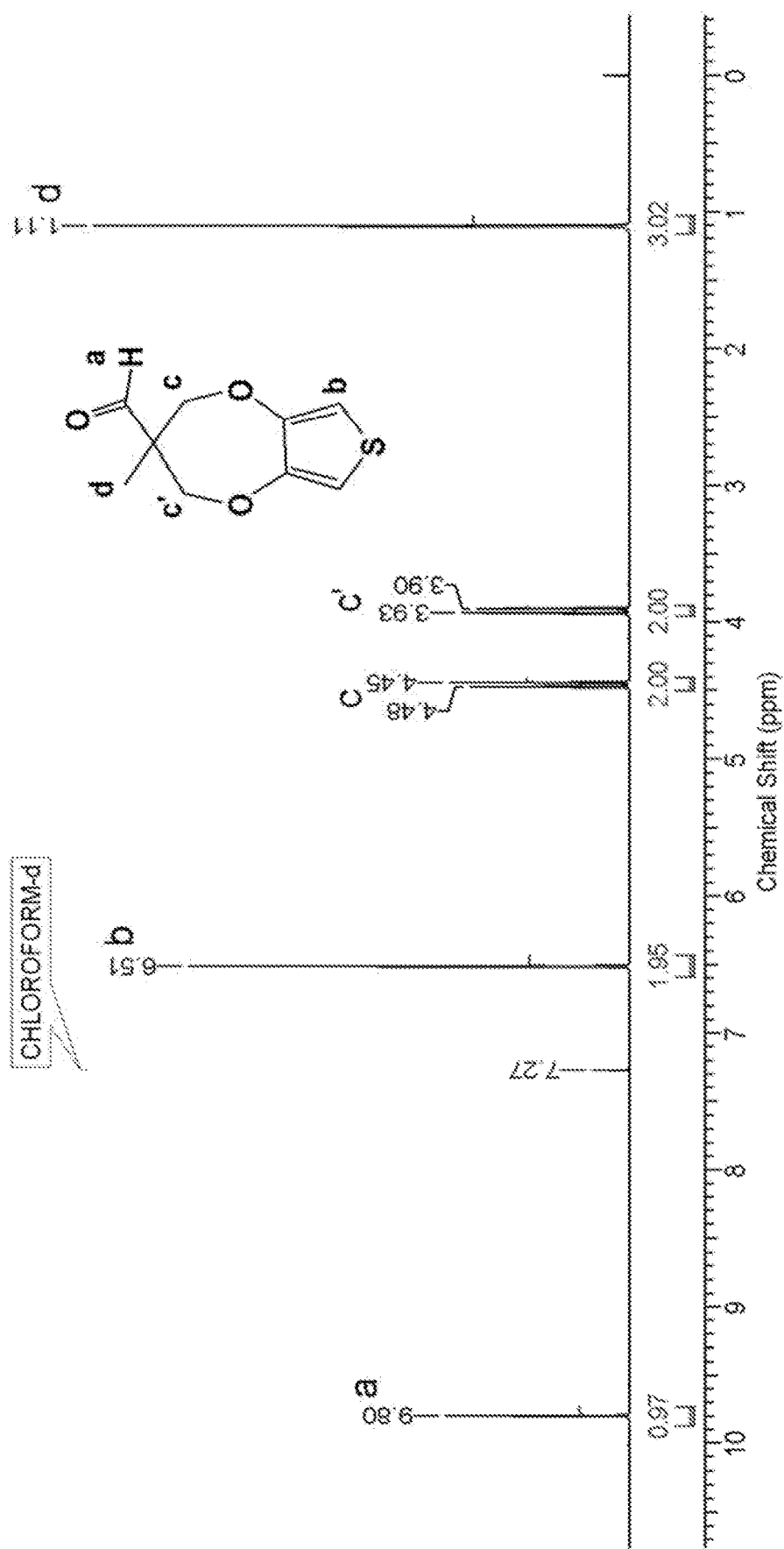
FIG. 2 displays $^1$H-NMR spectrum (in $CDCl_3$) of 3-methyl-3,4-dihydro-2H-thieno[3,4-b][1,4]dioxepine-3-carbaldehyde (ProDOT-aldehyde), according to embodiments of the present invention.

ProDOT-aldehyde was characterized by FT-IR, $^1$H NMR and $^{13}$C NMR and spectroscopy. $^1$H NMR spectrum, along with peak assignments, of the as-synthesized ProDOT-aldehyde is shown in FIG. 2. The spectrum was in good agreement with the proposed molecular structure of ProDOT-aldehyde.

$^1$H NMR (400 MHz, CDCl$_3$): δ=9.80 (s, 1H), 6.51 (s, 2H), 6.40 (d, 1H), 4.47 (d, 2H), 3.92 (d, 2H), 1.11 (s, 3H) $^{13}$C NMR: δ=202.4, 149.1, 106.0, 74.2, 54.1, 15.3 ppm.

Example No. 3

Synthesis of 2'-Maleimideomethyl-3,4-ethylenedioxythiophene (EDOT-MA)

Scheme 6 depicts route followed for the synthesis of EDOT-MA monomer starting from EDOT-NH$_2$. First, 3,4-dimethoxythiophene was converted into EDOT-NH$_2$ by the reported procedure (Hai et al., "Specific Recognition of Human Influenza Virus with PEDOT Bearing Sialic Acid-Terminated Trisaccharides," ACS Applied Materials & Interfaces, 2017, 9 (16): 14162-70). EDOT-NH$_2$ was then reacted with maleic anhydride in acetic acid to afford EDOT-MA.

Scheme 6

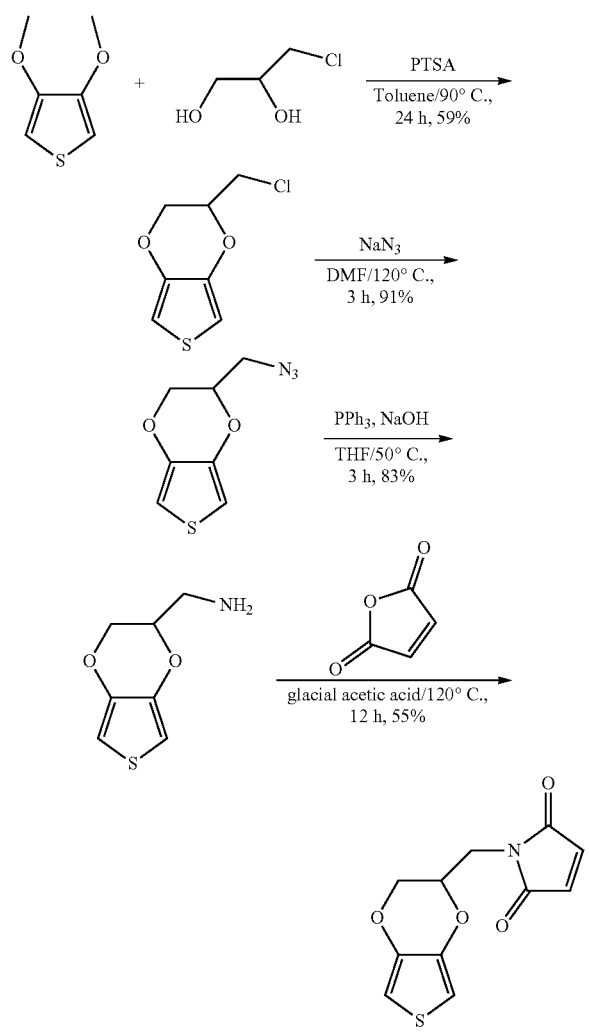

EDOT-MA

Step 3A: Synthesis of 2'-Chloroomethyl-3,4-ethylenedioxythiophene (EDOT-Cl)

Into a 500 mL two necked round-bottom flask equipped with a reflux condenser and argon inlet were placed, 3,4-dimethoxythiophene (10.0 g, 69.35 mmol), anhydrous toluene (250 mL) with 3-chloro-1,2-propanediol (13.16 mL, 157.44 mmol), and p-toluenesulfonic acid (p-TSA) (1.62 g, 6.935 mmol). The reaction mixture was stirred at 90° C. for 24 h. After this time, 3-chloro-1,2-propanediol (13.16 mL) were added to the reaction mixture which was stirred at 90° C. for further 3 h. The reaction mixture was allowed to cool to room temperature and the solvent was evaporated under reduced pressure. The solution of 10% sodium bicarbonate (150 mL) was added to the crude and the product was extracted with dichloromethane (3×100 mL). The organic phases were combined, washed with water (2×100 mL) and dried over anhydrous sodium sulfate, filtered and evaporated under reduced pressure. The crude product was purified by column chromatography using petroleum ether: dichloromethane (50:50, v/v) as an eluent to afford EDOT-Cl (7.85 g, 59%).

$^1$H NMR (400 MHz, CDCl$_3$): δ=6.38 (dd, 2H), 4.40-4.37 (m, 1H), 4.29 (dd, 1H), 4.17 (dd, 1H), 3.76-3.65 (m, 2H), $^{13}$C NMR: δ=141.1, 140.6, 100.1, 72.8, 65.5, 41.3 ppm.

Step 3B: Synthesis of 2'-Azidomethyl-3,4-ethylenedioxythiophene (EDOT-N$_3$)

Into a 100 mL two necked round-bottom flask equipped with argon inlet were added EDOT-Cl (3.0 g, 15.74 mmol) and N, N-dimethylformamide (50 ml). Sodium azide (2.05 g, 31.47 mmol) was added to the solution and the reaction mixture was stirred at 120° C. for 3 h. After cooling, the N, N-dimethylformamide was removed by rotary evaporation under reduced pressure. Then, water (200 mL) was added to the residue and the product was extracted with diethyl ether (2×150 mL). The solution dried over anhydrous sodium sulfate, filtered and evaporated under reduced pressure to afford EDOT-N$_3$ as a pale yellow oily liquid (2.82 g, 91%).

$^1$H NMR (400 MHz, CDCl$_3$): δ=6.39 (dd, 2H), 4.34-4.30 (m, 1H), 4.20 (dd, 1H), 4.05 (dd, 1H), 3.61-3.48 (m, 2H), $^{13}$C NMR: δ=141.0, 140.6, 100.2, 100.1, 72.4, 65.7, 50.5 ppm.

Step 3C: Synthesis of 2'-Aminomethyl-3,4-ethylenedioxythiophene (EDOT-NH$_2$)

Into a 50 mL two necked round-bottom flask equipped with a reflux condenser, a magnetic stirring bar were charged tetrahydrofuran (10 mL), EDOT-N$_3$ (1.0 g, 5.10 mmol), triphenylphosphine (1.6 g, 6.1 mmol) and 2 mol L$^{-1}$ sodium hydroxide aqueous solution (10 mL). The reaction mixture was stirred at 50° C. for 3 h. The reaction mixture was allowed to cool to room temperature. After evaporation of tetrahydrofuran, 2 M hydrochloric acid solution was used to control the pH below 3. Then the aqueous layer was extracted with dichloromethane (2×20 mL) and the combined organic layers were discarded. 1 M sodium hydroxide solution was added to adjust the pH of aqueous layer to 12. The aqueous layer was extracted with dichloromethane (3×20 mL) and the combined organic layers were dried with anhydrous sodium sulfate. The solvent was removed under reduced pressure to afford EDOT-NH$_2$ as colorless oil (0.72 g, 83%).

$^1$H NMR (400 MHz, CDCl$_3$): δ=6.33 (dd, 2H), 4.20 (dd, 1H), 4.12 (m, 1H), 4.00 (dd, 1H), 2.97 (m, 2H), 1.32 (s, 2H) $^{13}$C NMR: δ=141.6, 140.5, 99.5, 75.2, 66.6, 42.3 ppm.

Step 3D: Synthesis of 2'-Maleimideomethyl-3,4-ethylenedioxythiophene (EDOT-MA)

Into a 50 mL two necked round-bottom flask equipped with a mechanical stirrer, a gas inlet and a reflux condenser were placed EDOT-NH$_2$ (0.20 g, 1.16 mmol), maleic anhydride (0.138 g, 1.40 mmol) and glacial acetic acid (10 mL). The reaction mixture was stirred at 120° C. for 12 h. The reaction mixture was cooled to room temperature and glacial acetic acid removed by evaporation under reduced pressure. The crude product was dissolved in ethyl acetate and the solution was washed with water (3×20 mL). The ethyl acetate solution was dried over anhydrous sodium sulfate, filtered and ethyl acetate was removed by evaporation under reduced pressure. The crude product was purified by column chromatography using petroleumether: ethyl acetate (70:30, v/v) as an eluent to afford pure EDOT-MA (0.16 g, 55%).

Figure 3:
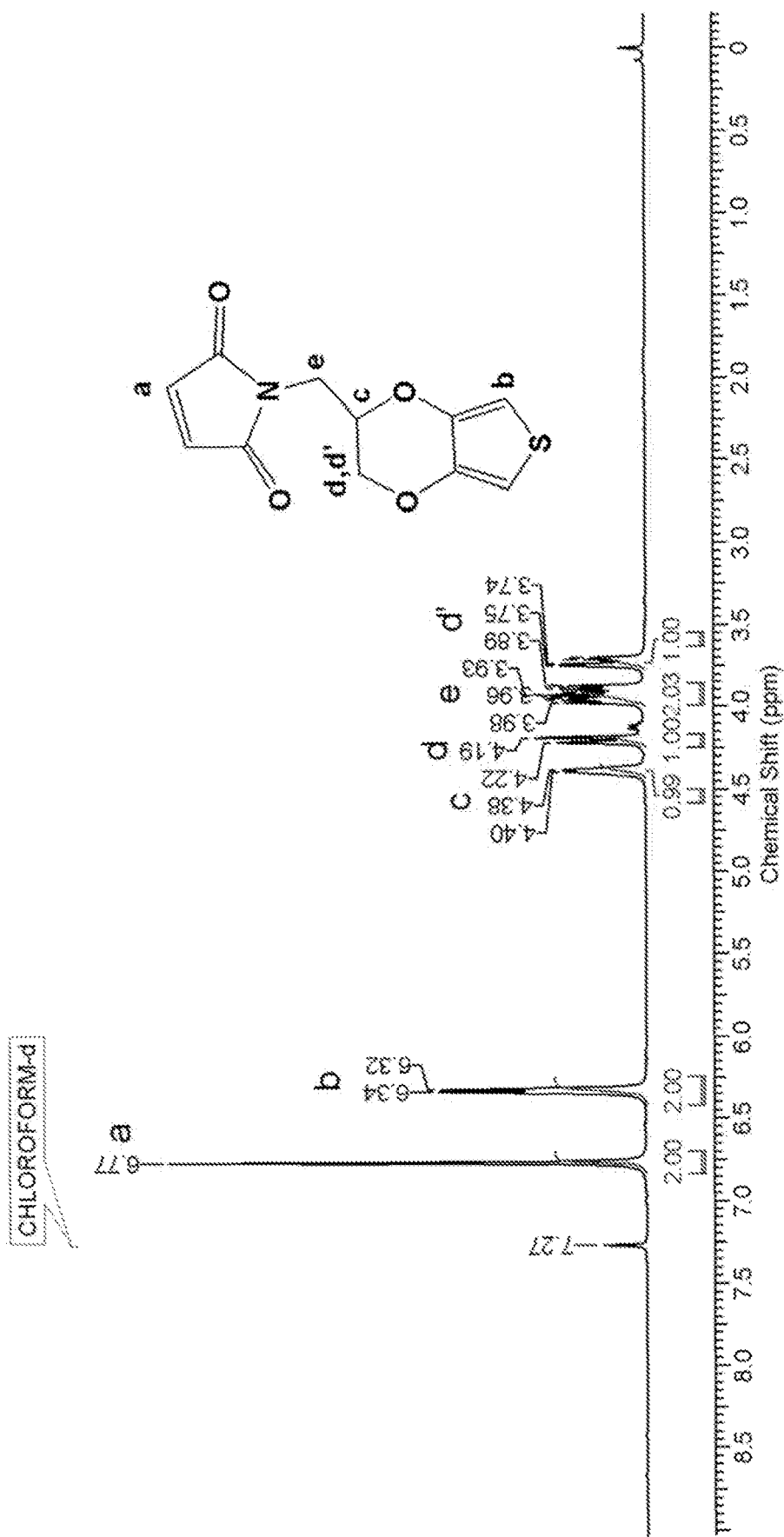
FIG. 3 displays $^1$H-NMR spectrum (in $CDCl_3$) of 2'-Maleimideomethyl-3,4-ethylenedioxythiophene (EDOT-MA), according to embodiments of the present invention.

EDOT-MA was characterized by FT-IR, $^1$H NMR and $^{13}$C NMR spectroscopy. The $^1$H NMR spectrum of EDOT-MA is illustrated in FIG. 3. The characteristics peak of vinyl protons of maleimide was observed at 6.77 δ ppm which indicated the successful synthesis of the EDOT containing maleimide group. The spectral data for other protons were in good agreement with the proposed structure.

$^1$H NMR (400 MHz, CDCl$_3$): δ=6.77 (s, 2H), 6.33 (d, 2H), 4.39 (d, 1H), 4.21 (d, 1H), 3.98-3.88 (m, 2H), 3.73 (dd, 1H), $^{13}$C NMR: δ=170.2, 141.0, 134.3, 100.2, 70.9, 66.1, 37.7 ppm.

Example No. 4

Synthesis of N-(3,4-dihydroxyphenethyl)-2,3-dihydrothieno[3,4-b][1,4]dioxine-2-carboxamide (EDOT-dopamide)

Scheme 7 outlines the synthesis of EDOT-dopamide by reaction of EDOT-acid with dopaminein the presence of DIPEA and HATU at room temperature.

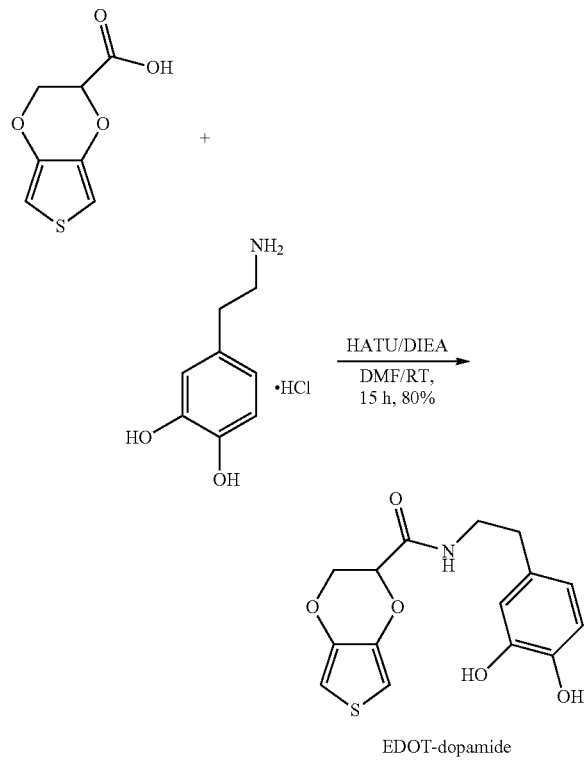

Scheme 7

Into a 100 mL two necked round-bottom flask equipped with a magnetic stirrer and argon gas inlet were placed EDOT-COOH (1.0 g, 5.37 mmol), anhydrous N, N-dimethylformamide (50 mL). Diisopropylethylamine (DIPEA) (3.08 mL, 17.72 mmol) and 1-[Bis(dimethylamino)methylene]-1H-1,2,3-triazolo[4,5-b]pyridinium 3-oxide hexafluorophosphate (HATU) (2.25 g, 5.91 mmol) were added together at room temperature. After 30 minutes 3,4-dihydroxyphenethylamine (Dopamine) 1.53 g, 8.06 mmol) has been added and let stirred overnight at room temperature. After, N, N-dimethylformamide was removed under reduced pressure and the crude product dissolves in ethyl acetate (100 mL). The organic phase was washed with water (3×100 mL), dried over sodium sulfate and the solvent remove under vacuum. The crude product was purified by column chromatography using petroleum ether: ethyl acetate (80:20, v/v) as an eluent to afford EDOT-dopamide (0.68 g, 80%).

Figure 4:
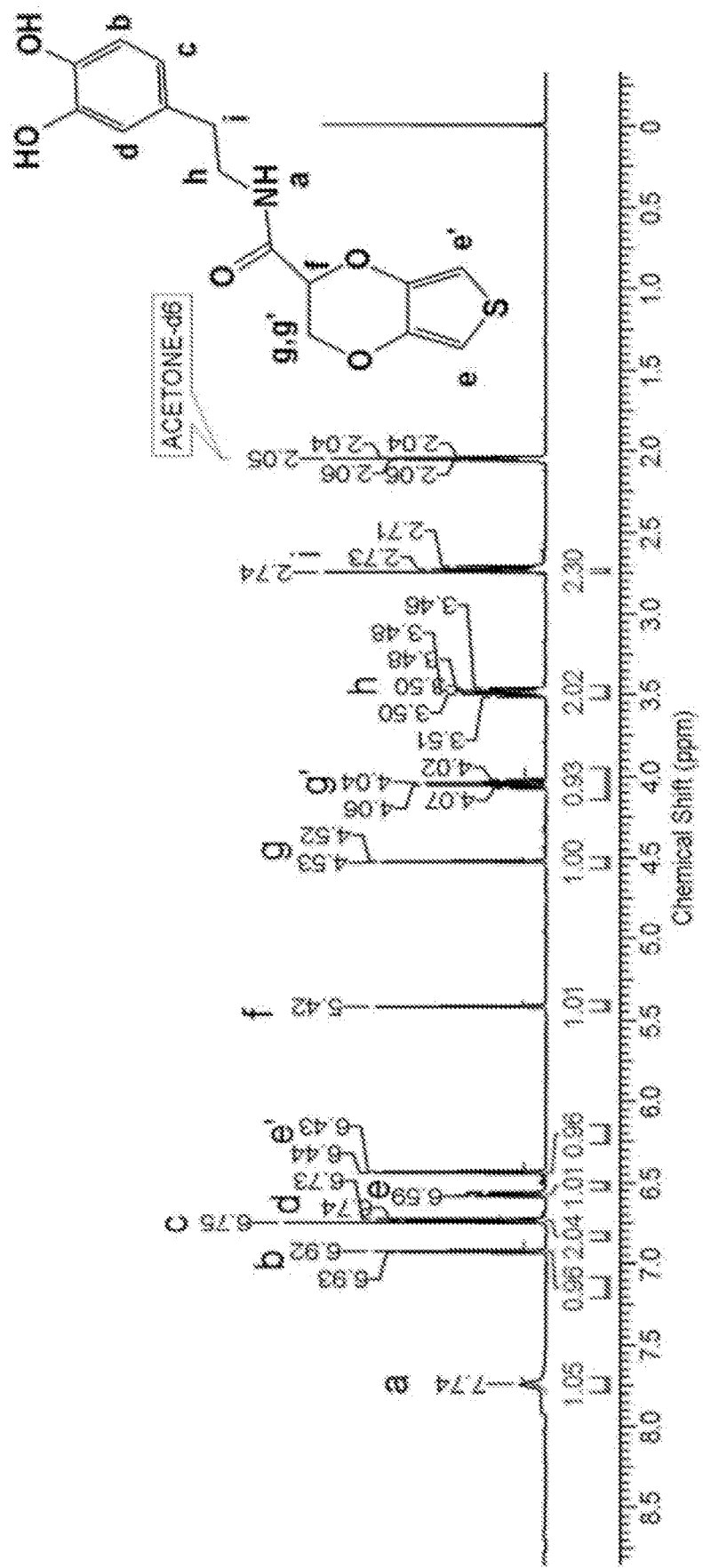
FIG. 4 displays $^1$H-NMR spectrum (in Acetone-$d_6$) of N-(3,4-dihydroxyphenethyl)-2,3-dihydrothieno[3,4-b][1,4]dioxine-2-carboxamide (EDOT-dopamide), according to embodiments of the present invention.

The chemical structure of EDOT-dopamide was confirmed by FT-IR, $^1$H NMR and $^{13}$C NMR spectroscopy. $^1$H NMR spectrum of the as-synthesized EDOT-dopamide exhibited the signals at 6.93 and 6.75 δ ppm which correspond to phenolic aromatic protons. Assignment of remaining protons is depicted in FIG. 4 and spectrum agreed well with the proposed molecular structure of EDOT-dopamide.

$^1$H NMR (400 MHz, Acetone-d$_6$): δ=7.74 (s, 1H), 6.93 (d, 1H), 6.75 (d, 1H), 6.73 (s, 1H), 6.58 (dd, 1H), 6.44 (d, 1H), 5.42 (d, 1H), 4.53 (d, 1H), 4.06 (dd, 1H), 3.51-3.46 (m, 2H), 2.73 (t, 2H) $^{13}$C NMR: δ=162.1, 147.1, 145.9, 144.1, 142.2, 131.9, 120.9, 116.6, 116.1, 110.7, 100.5, 95.4, 60.6, 42.0, 35.8 ppm.

Example No. 5

Synthesis of EDOT-tyramine

Scheme 8 shows synthesis of an EDOT containing tyramine starting from EDOT-N$_3$ and Tyramine-MA via metal-free 1, 3-dipolar azide-maleimide cycloaddition click reaction in dry chloroform at 60° C. for 12 h.

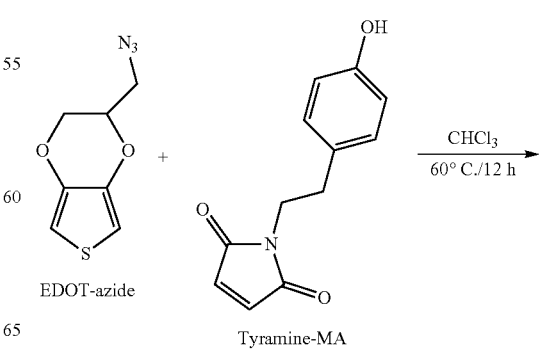

Scheme 8

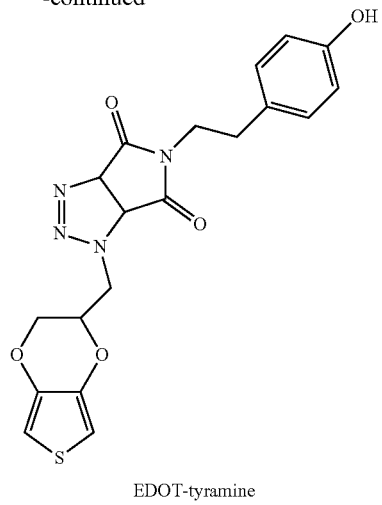

EDOT-tyramine

Into a 50 mL necked round-bottom flask equipped with a mechanical stirrer, a gas inlet and a reflux condenser were added EDOT-N$_3$ (0.20 g, 1.01 mmol), tyramine-MA (0.241 g, 1.11 mmol) and dry chloroform (10 mL). The reaction mixture was stirred at 60° C. under nitrogen atmosphere for 12 h. The reaction mixture was cooled to room temperature and chloroform removed by evaporation under reduced pressure. The crude product was dissolved in ethyl acetate and the solution was washed with water (2×30 mL). The ethyl acetate solution was dried over anhydrous sodium sulfate, filtered and ethyl acetate was removed by evaporation under reduced pressure. The crude product was purified by column chromatography using petroleumether: ethyl acetate (80:20, v/v) as an eluent to afford pure EDOT-Tyramine (0.308 g, 70%). Melting point (DSC) was 145.1° C. FT-IR spectrum showed following peaks: 3225, 1704, 1614, 1596, 1515, cm$^{-1}$.

Figure 5:
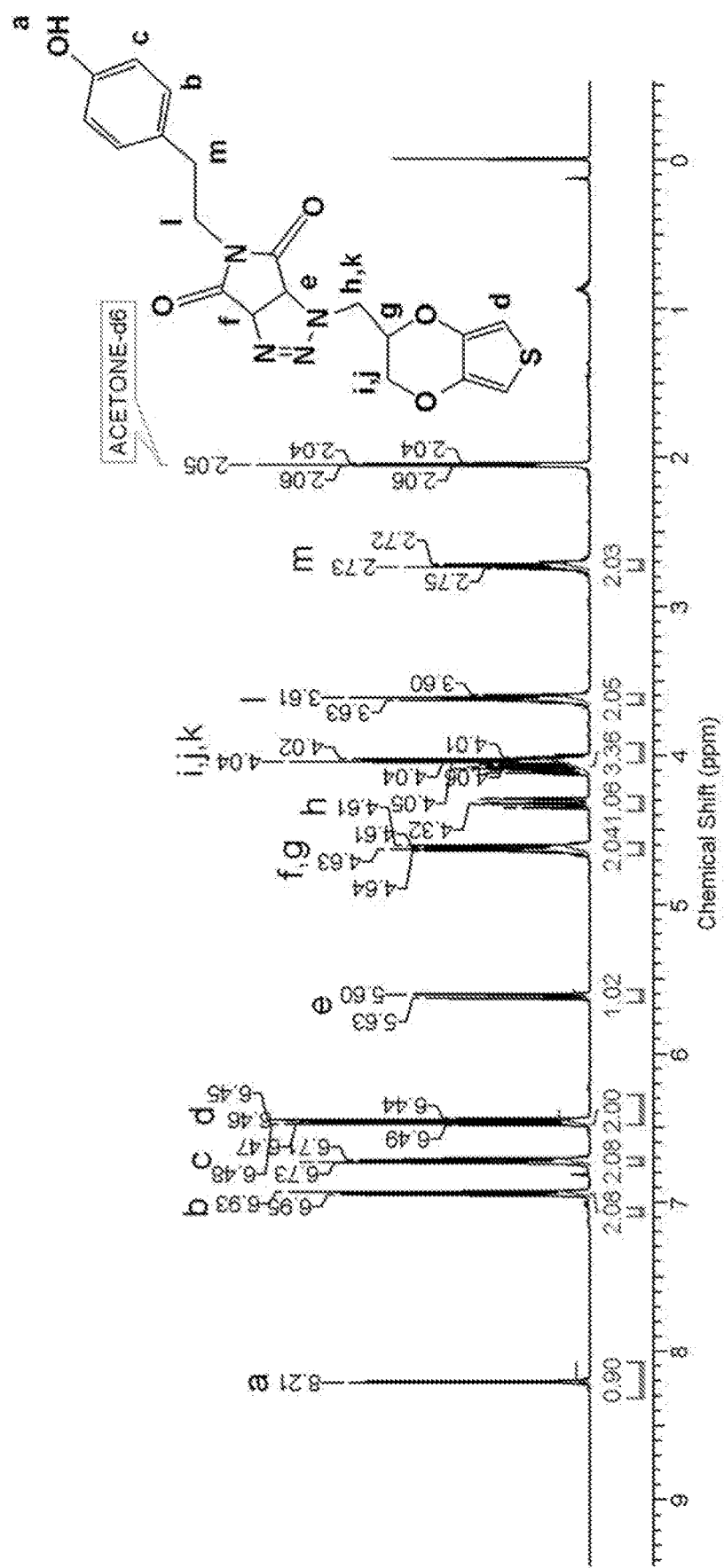
FIG. 5 displays $^1$H-NMR spectrum (in $CDCl_3$) of EDOT-tyramine, according to embodiments of the present invention.

The chemical structures of EDOT-tyramine was confirmed by FT-IR, $^1$H-NMR and $^{13}$C-NMR spectroscopy. $^1$H NMR spectrum of EDOT-tyramine, along with assignments of the protons, is shown in FIG. 5.

$^1$H NMR (400 MHz, Acetone-d$_6$): δ=8.21 (s, 1H), 6.48 (d, 2H), 6.72 (dd, 2H), 6.49-6.44 (m, 2H), 5.62 (dd, 1H), 4.64-4.62 (dd, 2H), 4.36-4.29 (m, 1H), 4.12-4.01 (m, 3H), 3.61 (t, 2H), 2.73 (t, 2H); $^{13}$C NMR (100 MHz, Acetone-d$_6$): δ=173.3, 171.6, 157.0, 142.5, 130.7, 129.3, 116.2, 100.5, 83.6, 73.05, 66.7, 60.5, 49.5, 41.0, 32.9 ppm.

Example No. 6

Synthesis of 2'-Carbaldehyde-3,4-ethylenedioxythiophene (EDOT-cholesterol)

EDOT containing cholesterol was readily synthesized in one-step reaction by condensation of EDOT-acid with cholesterol in the presence of EDCI and DMAP at room temperature, as shown below in Scheme 9.

Scheme 9

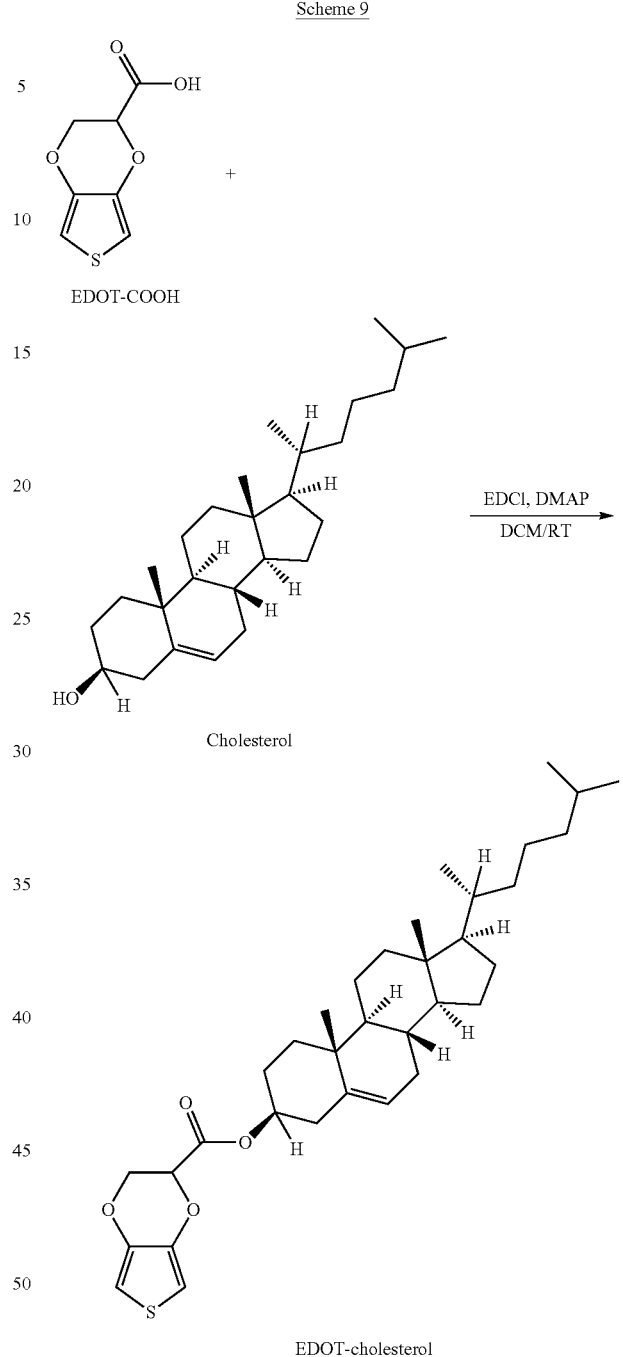

EDOT-cholesterol

Into aInto a 100 mL two necked round-bottom flask equipped with a mechanical stirrer and a nitrogen inlet were added EDOT-COOH (0.20 g, 1.07 mmol), cholesterol (0.415 g, 1.07 mmol) and dichloromethane (20 mL). DMAP (0.131 g, 1.07 mmol) was added to the reaction mixture and stirred at ambient temperature. After 10 min, EDCI (0.412 g, 2.14 mmol) was added to the reaction mixture in one portion. The mixture was stirred overnight at room temperature. Then the mixture was extracted with dichloromethane (3×30 mL) and washed with brine. The combined organic layers were dried by sodium sulfate and evaporated under vacuum to give crude product, which was purified by silica-gel column chromatography using petroleum ether: ethyl acetate (95:5, v/v) to obtain the EDOT-cholesterol (0.472 g, 77%). Melting point (DSC) was 161.1° C.

Figure 6:
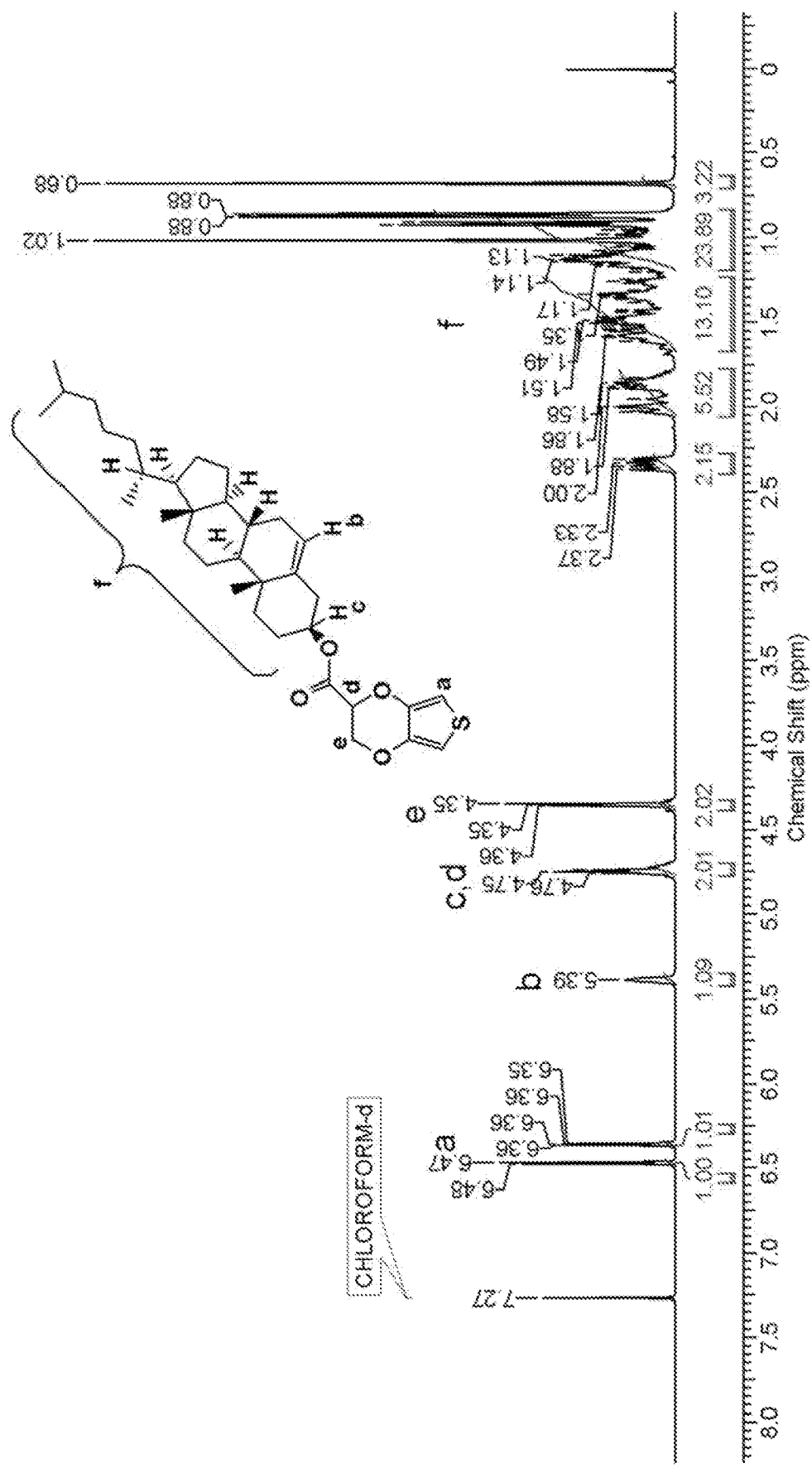
FIG. 6 displays $^1$H-NMR spectrum (in $CDCl_3$) of EDOT-cholesterol, according to embodiments of the present invention.

The chemical structures were elucidated on the basis of FT-IR, $^1$H NMR and $^{13}$C NMR spectroscopy. Assignment of protons in the $^1$H NMR spectrum is depicted in FIG. 6 and the $^1$H NMR spectrum agreed well with proposed molecular structure of EDOT-cholesterol. The FT-IR spectrum showed peaks at: 1760 and 1706 cm$^{-1}$.

$^1$H NMR (400 MHz, Acetone-d$_6$): δ=6.48 (d, 1H), 6.36 (dd, 1H), 5.39 (s, 1H), 4.75 (m, 2H), 4.35 (d, 2H), 2.23 (q, 2H), 2.03-1.83 (m, 5H), 1.61-1.25 (m, 13H), 1.17-0.86 (m, 23H), 0.86 (s, 3H); $^{13}$C NMR (100 MHz, Acetone-d$_6$): δ=167.1, 140.5, 139.0, 123.2, 100.3, 75.9, 72.2, 65.6, 56.5, 49.9, 42.3, 39.5, 37.8, 36.8, 36.5, 36.1, 35.8, 31.8, 28.2, 28.0, 27.6, 24.2, 23.8, 22.8, 22.5, 21.0, 19.3, 18.7, 11.8 ppm.

Example No. 7

Synthesis of EDOT-MA Derivatives

Derivatives of EDOT-MA containing adamantane, cholesterol or cystein can be readily synthesized in one-step reaction of EDOT-MA with a derivative containing thiol group in the presence of TEA and DCM at room temperature for adamantane or cholesterol or in the presence of DMSO for derivative of cysteine, as shown below in Scheme 10.

Scheme 10

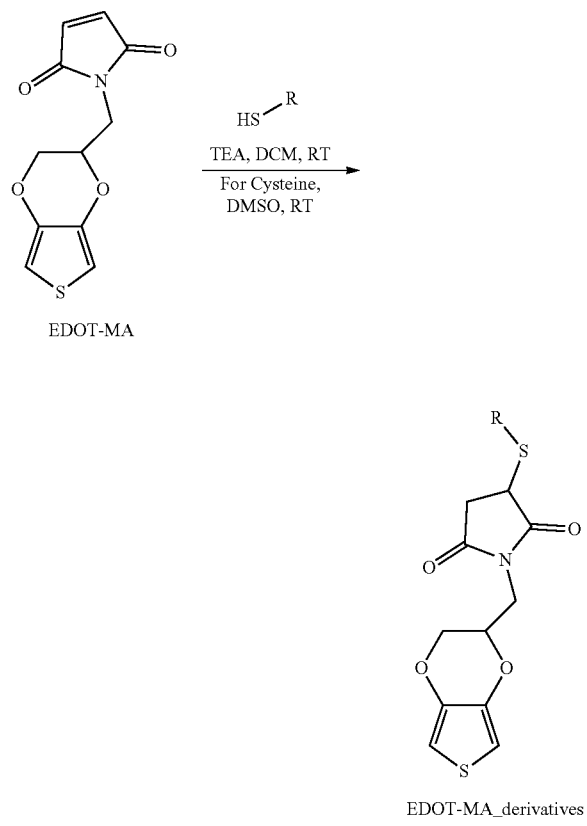

EDOT-MA_derivatives

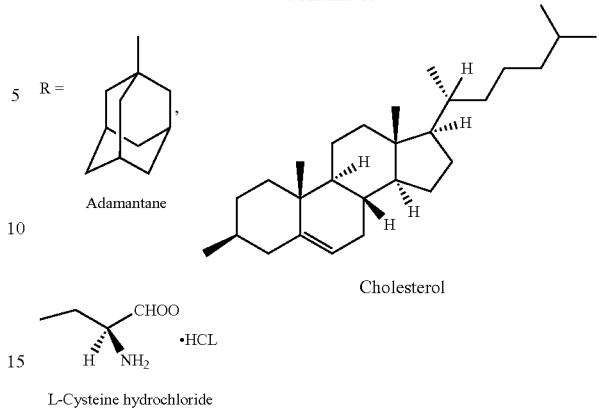

L-Cysteine hydrochloride

Example 7A

Synthesis of EDOT-MA Adamantane

Into a round bottom flask equipped with a magnetic stirring bar were added EDOT-MA (0.20 g, 0.80 mmol), 1-adamantanethiol (0.135 g, 0.80 mmol), triethylamine (111 μL, 0.80 mmol), and dry dichloromethane (5 mL). The reaction mixture was stirred at room temperature under nitrogen atmosphere for 8 h. The dichloromethane (20 mL) was added to the reaction mixture and the solution was washed with water (3×20 mL). The solution was dried over anhydrous sodium sulfate, filtered and dichloromethane was removed by evaporation under reduced pressure. The crude product was purified by column chromatography using pet ether: ethyl acetate (80:20, v/v) as an eluent to afford pure EDOT-MA_adamantane.

$^1$H NMR (400 MHz, CDCl$_3$): δ=6.34 (d, 2H), 4.41 (t, 1H), 4.21-4.17 (m, 1H), 3.99-3.87 (m, 3H), 3.73-3.67 (m, 1H), 3.30-3.22 (m, 1H), 2.75-2.67 (m, 1H), 2.11 (s, 3H), 1.95 (s, 6H), 1.72 (s, 6H); $^{13}$C NMR (100 MHz, CDCl$_3$): δ=176.9, 174.6, 141.0, 140.6, 100.3, 99.9, 70.4, 66.3, 47.3, 43.7, 43.0, 39.2, 39.1, 36.0, 30.0, 29.7 ppm.

Example No. 7B

Synthesis of EDOT-MA Cholesterol

Into a round bottom flask equipped with a magnetic stirring bar were added EDOT-MA (0.20 g, 0.80 mmol), thiocholesterol (0.321 g, 0.80 mmol), triethylamine (111 μL, 0.80 mmol), and dry dichloromethane (5 mL). The reaction mixture was stirred at room temperature under nitrogen atmosphere for 8 h. The dichloromethane (20 mL) was added to the reaction mixture and the solution was washed with water (3×20 mL). The solution was dried over anhydrous sodium sulfate, filtered and dichloromethane was removed by evaporation under reduced pressure. The crude product was purified by column chromatography using pet ether: ethyl acetate (80:20, v/v) as an eluent to afford pure EDOT-MA_cholesterol.

$^1$H NMR (400 MHz, CDCl$_3$): δ=6.34 (m, 2H), 5.37 (s, 1H), 4.42 (t, 1H), 4.22-4.18 (m, 1H), 3.99-3.88 (m, 3H), 3.74-3.67 (m, 1H), 3.24-3.16 (m, 1H), 3.08 (d, 1H), 2.63-2.56 (m, 1H), 2.27 (m, 1H), 2.03-1.82 (m, 5H), 1.60-0.86 (m, 40H), 0.68 (s, 3H); $^{13}$C NMR (100 MHz, CDCl$_3$): δ=176.4, 175.5, 141.0, 140.8, 140.5, 121.8, 100.4, 99.9, 70.4, 66.2, 56.7, 50.1, 44.8, 42.2, 40.0, 39.7, 39.5, 38.8, 37.7, 36.7, 36.5, 36.1, 35.7, 31.8, 29.8, 29.1, 28.2, 28.0, 24.2, 23.8, 22.8, 22.5, 20.9, 19.3, 18.7, 11.8 ppm.

Example No. 7C

Synthesis of EDOT-MA Cysteine

Into a 25 mL two necked round-bottom flask fitted with a magnetic stirring bar were added EDOT-MA (0.200 g, 0.80 mmol), L-cysteine hydrochloride (0.126 g, 0.80 mmol) and dimethyl sulfoxide (5 mL). The reaction mixture stirred at room temperature for 8 h, while consumption of starting material was monitored by TLC. After the reaction was complete DMSO evaporated under reduced pressure to afford EDOT-MA_cysteine.

$^1$H NMR (400 MHz, DMSO-$d_6$): δ=8.61 (s, 3H), 6.61-6.55 (m, 2H), 4.32 (m, 1H), 4.23 (m, 1H), 3.98-3.93 (m, 1H), 3.71-3.62 (m, 2H), 3.46-3.41 (m, 2H), 3.30 (d, 2H), 2.71-2.60 (m, 2H); $^{13}$C NMR (100 MHz, DMSO-$d_6$): δ=177.0, 174.8, 169.4, 141.0, 140.7, 100.2, 100.0, 70.3, 65.8, 52.1, 51.5, 38.3, 35.8, 31.4 ppm Example No. 8

Electrochemical Polymerization

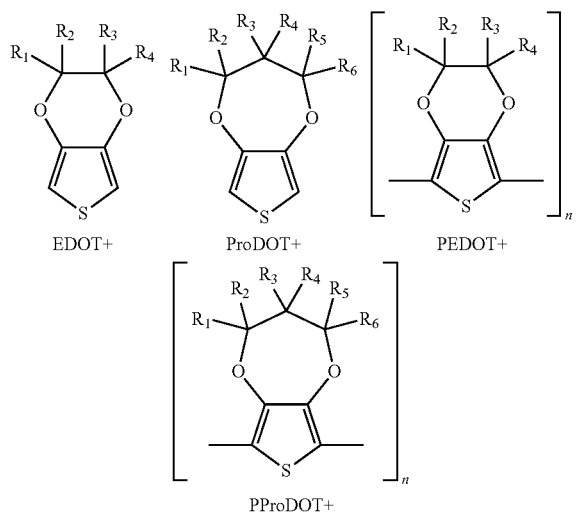

Each of the monomers of Examples 1-7 has shown the ability to be electrochemically deposited onto substrates, although the efficiency of film deposition is clearly a function of chemistry and the composition of the solvent used, and composition of the electrode. Typically, water was used as the deposition solvent, since it is readily available and is ubiquitous in biological systems. Additionally, it was found that adding small amounts of propylene carbonate (PPC) to water created a binary solvent mixture (around 88 water: 12 PPC) that is particularly effective in assisting in film formation. While not bound by any specific theory, it is believed that the PPC helps to solubilize the monomer, yet still allows for precipitation of the polythiophene film as the molecular weight increases.

Polymerization of EDOT and functional EDOT's was done Polymerization of monomers was done using electrochemical methods by either potentiostatic or galvanostatic control. Solutions were made with a monomer concentration of 0.01 M and lithium perchlorate (LiClO$_4$) counterion concentration of 0.02 M in the desired solvent. For polymerizations in homosolvent, the monomer was added directly to the solvent for solvation. In many cases a binary solvent mixture of 88% DI water and 12% propylene carbonate (PPC) by volume was found to work well in solvating the monomers and not the resulting polymers which allowed for film formation upon the applied potential. The binary solvent was first mixed by vortexing and then the monomer was added.

Sonication of monomers was required to break apart monomer clumps and crystals for better dissolution. Complete solvation was not always achieved and a partially cloudy solution may remain, but enough monomer dissolves for polymerization. Vortexing of monomer solutions prior to deposition is essential to ensure that both solvents and monomers are uniformly distributed. Polymerization potentials were determined using cyclic voltammetry and from this the polymerization potential was used to form polymer films on the working electrode.

Figure 7:
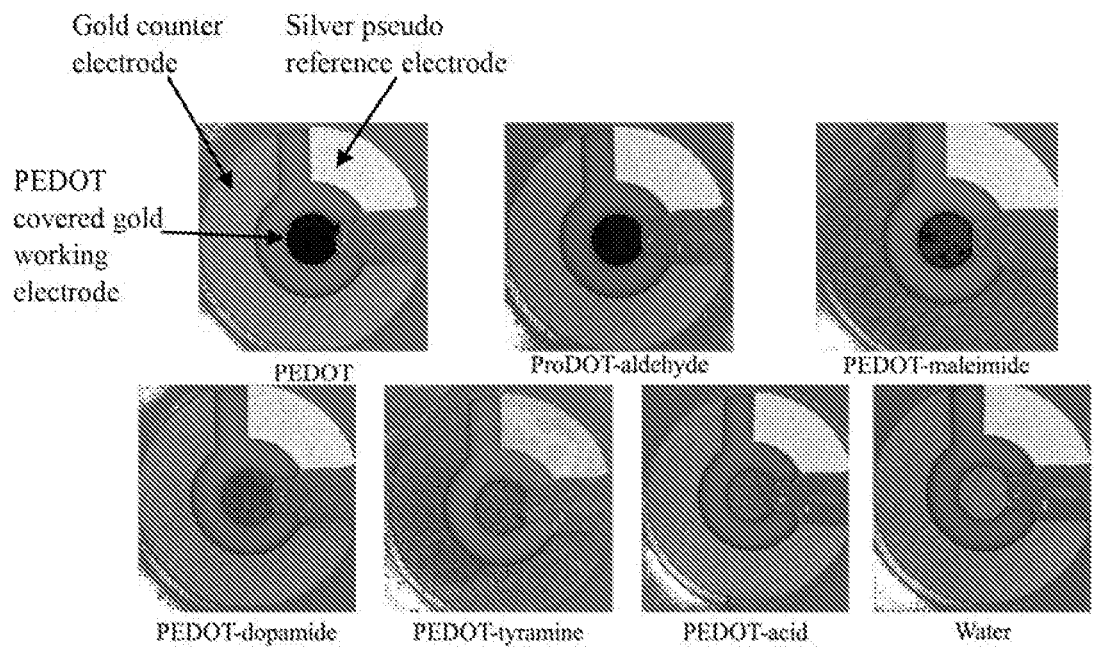
FIG. 7 displays Functional PEDOTs with decreasing thickness of conjugated polymer films, according to embodiments of the present invention.

For a polymerization a 50 μL drop of monomer solution was dropped onto the electrode surface, completely covering the three electrodes. The electrodes used were composed of a 1.6 mm diameter gold working electrode, a gold counter electrode and a silver pseudo reference electrode, as shown in FIG. 7. A charge density of 1.5 MC/mm$^2$ was used for polymerization with a current of 10 μA/mm$^2$ for 150 seconds on Dropsens commercially available screen printed electrodes 223AT.

Table 1 lists a portion of the already synthesized EDOT+ derivatives, polymerization solvent, and polymerization potentials for those specific solvents.

TABLE 1

| Monomer | Solvent | Polymerization Potential (V) vs. SHE |
| --- | --- | --- |
| EDOT | 88:12 Water:PPC by volume | 0.99 |
| EDOT-aldehyde | 88:12 Water:PPC by volume | 1.39 |
| EDOT-dopamide | 88:12 Water:PPC by volume | 0.84 |
| EDOT-tyramine | 88:12 Water:PPC by volume | 1.19 |
| EDOT-maleimide | 88:12 Water:PPC by volume | 1.09 |
| EDOT-adamantane | Acetonitrile | 1.27 |
| EDOT-cholesterol | PPC | 1.94 |
| EDOT-cysteine | Acetonitrile | 1.59 |
| ProDOT-aldehyde | 88:12 Water:PPC by volume | 1.09 |

FIG. 7 shows a series of functionalized polythiophenes electrochemically deposited onto a 1.6 mm diameter gold working screen-printed electrode (available from Metrohm DropSens, 223AT) using 0.2 uA/cm$^2$ of current for 150 seconds, corresponding a charge density of 0.15 C/cm$^2$. The films appeared to have a dark blue-black color similar to that of unmodified PEDOT. Without wishing to be bound by any particular theory, it is believed that the thickness of the film is a function of the monomer composition, presumably due to the change in solubility of the resulting polymer in solvent mixture as the side group becomes more hydrophilic, and thus there is less driving force for precipitation from solution.

Figure 8:
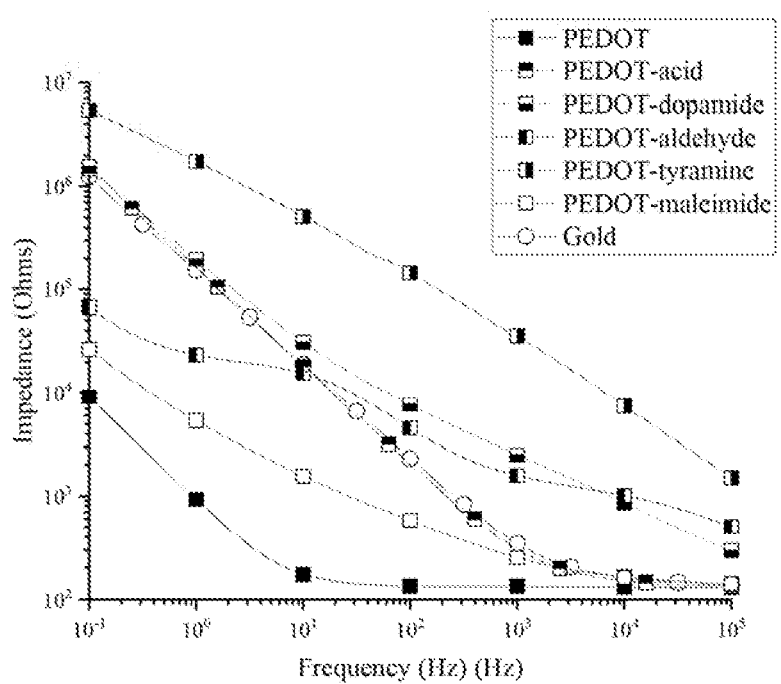
FIG. 8 displays electrochemical impedance spectra of functionalized polythiophenes prepared from the monomers disclosed hereonabove, according to embodiments of the present invention.

Polymerization potential varied significantly for different functional monomers with the three thickest films requiring the lowest potentials. Deposition of electrically active polythiophene films was confirmed through the change in color of the electrode surface as well as systematic changes the frequency dependent impedance spectra, as shown in FIG. 8. The changes in both magnitude and phase were highly dependent on the functional monomer used with some functional polymers showing electrical performances similar to regular PEDOT, with others showing more insulating behaviour. These new monomers make it possible for us to tune the chemical composition and corresponding properties of the resulting thiophene copolymers for specific applications.

Figure 9A:
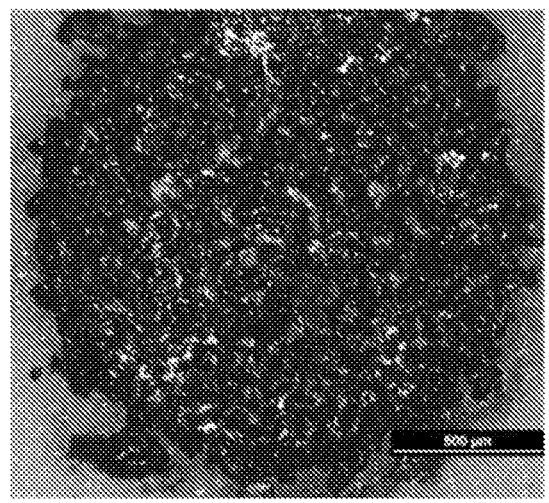
FIG. 9A shows an optical micrograph of a functional PEDOT-maleimide film, according to embodiments of the present invention.
Figure 9B:
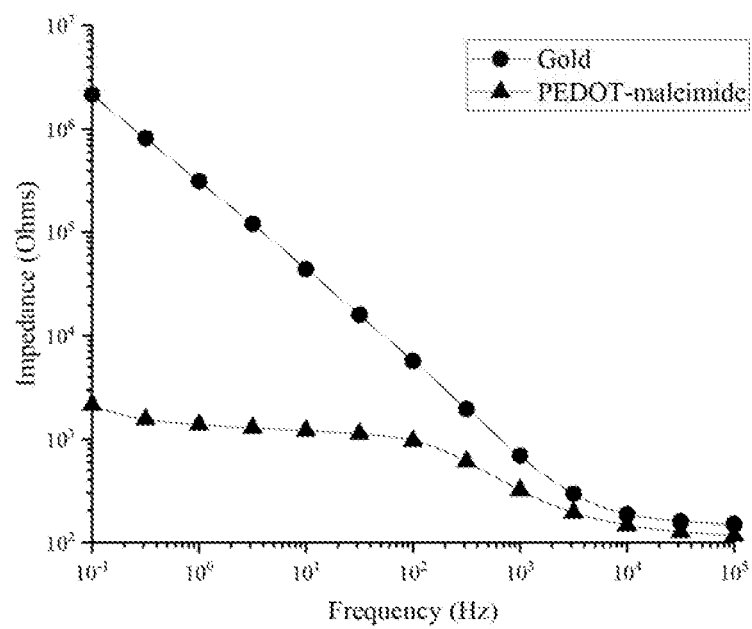
FIG. 9B shows a Bode plot of a functional PEDOT-maleimide film, according to embodiments of the present invention.

FIG. 9A shows an optical micrograph of a thick, dark film of poly(EDOT-MA) grown potentiostatically. The surface shows a rough morphology that correlates with low impedance seen in the EIS data, as shown in FIG. 9B. These films were found to deposit readily and were highly adherent to the gold electrode.

Figure 10:
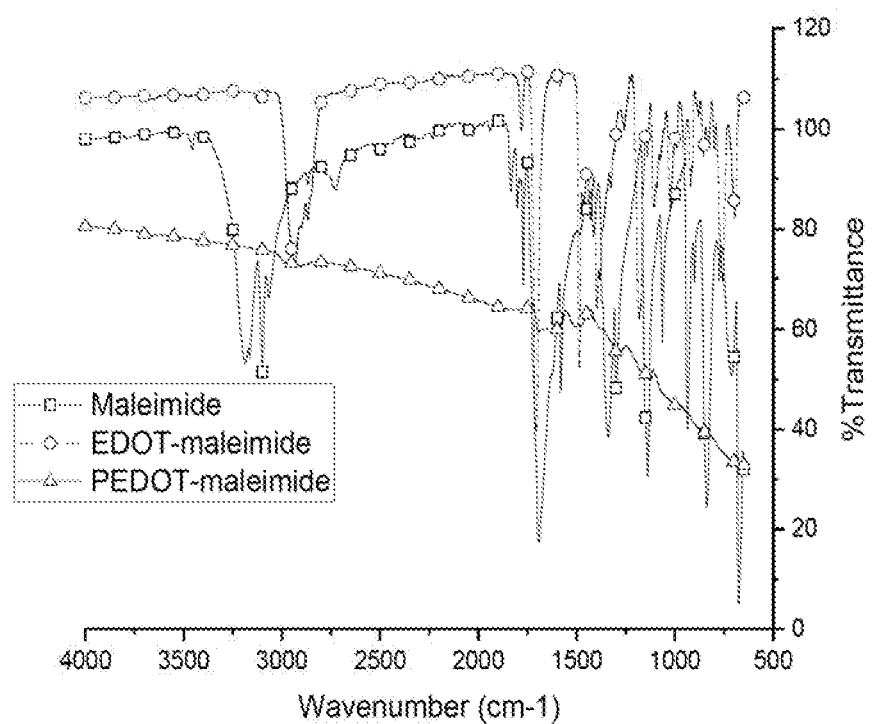
FIG. 10 shows Infra-red spectra of maleimide, a functionalized EDOT, which is a derivative of maleimide (EDOT-maleimide) and a corresponding electrodeposited functionalized polymer of the monomer EDOT-maleimide (PEDOT-maleimide), according to embodiments of the present invention.

FIG. 10 shows Infra-red spectra of maleimide, a functionalized EDOT, which is a derivative of maleimide (EDOT-maleimide) and a corresponding electrodeposited functionalized polymer of the monomer EDOT-maleimide (PEDOT-maleimide), according to embodiments of the present invention. Attachment of EDOT to maleimide causes a peak shift from 3180 cm$^{-1}$ to 2920 cm$^{-1}$ which is preserved, but is less pronounced in the polymer, PEDOT-maleimide. With polymerization comes a wide range of infrared absorption that makes only strong peaks such as those at 2920 cm$^{-1}$, 1710 cm$^{-1}$, and 1485 cm$^{-1}$ partially visible holdovers from the monomer.

Figure 11:
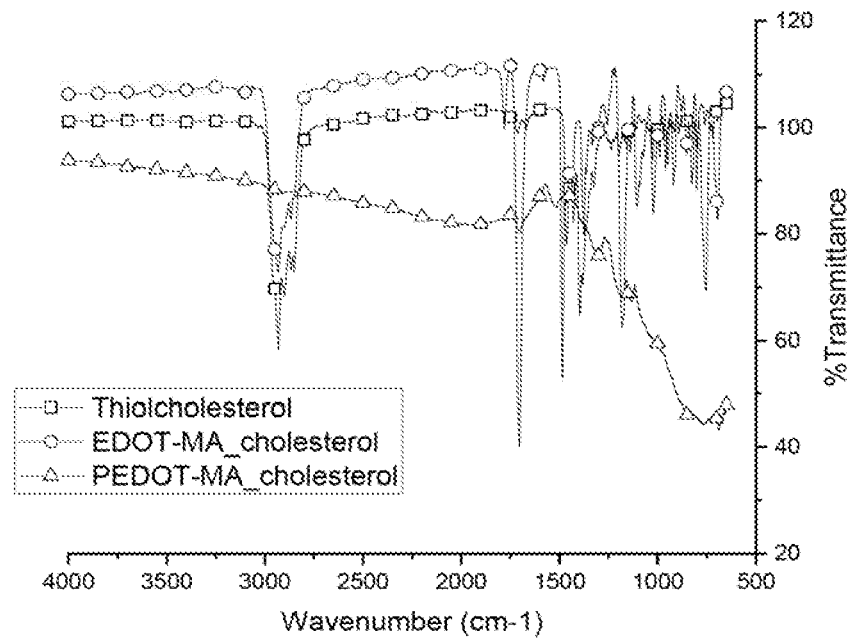
FIG. 11 shows Infra-red spectra of thiocholesterol, a functionalized EDOT, which is a derivative of thiolcholesterol (EDOT-MA_cholesterol) and a corresponding electrodeposited functionalized polymer of the monomer EDOT-MA_cholesterol (PEDOT-MA_cholesterol), according to embodiments of the present invention.

FIG. 11 shows Infra-red spectra of thiocholesterol, a functionalized EDOT, which is a derivative of thiolcholesterol (EDOT-MA_cholesterol) and a corresponding electrodeposited functionalized polymer of the monomer EDOT-MA_cholesterol (PEDOT-MA_cholesterol), according to embodiments of the present invention. Post modification and post polymerization the peaks at 2930 cm$^{-1}$, 1705 cm$^{-1}$ are partially visible, but due to polymerization are not as distinguishable as in the monomer.

Figure 12:
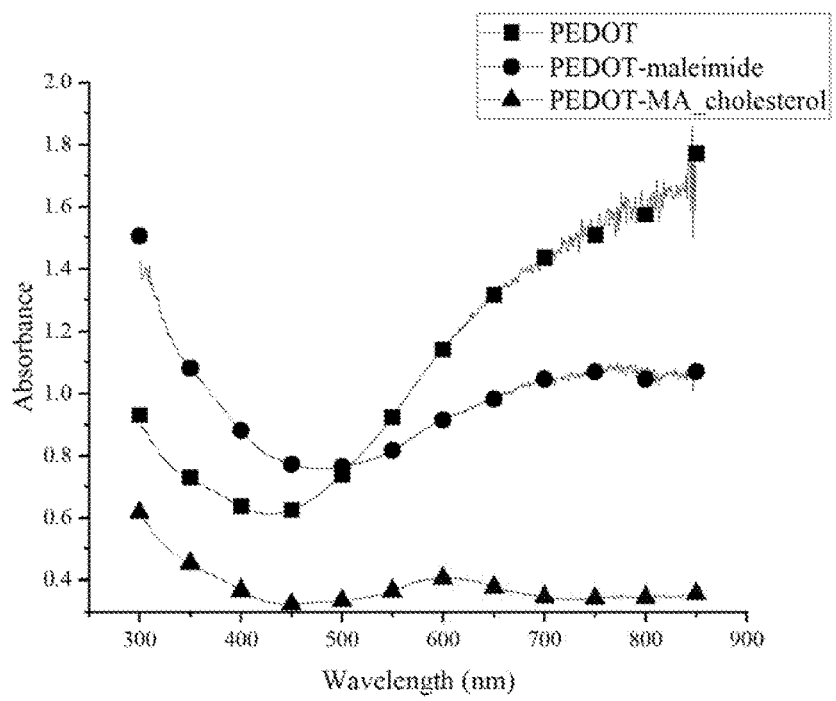
FIG. 12 shows absorption spectra in the UV-Visible range of electrodeposited functionalized polymers of EDOT and EDOT+: PEDOT, PEDOT-maleimide, and PEDOT-MA_cholesterol, according to embodiments of the present invention.

FIG. 12 shows absorption spectra in the UV-Visible range of electrodeposited functionalized polymers of EDOT and EDOT+: PEDOT, PEDOT-maleimide, and PEDOT-MA_cholesterol, according to embodiments of the present invention. Both derivatives shown have broad absorption over a wide range of wavelengths with a noted increase starting at 500 nm which corresponds to the conjugation of the polymer. Differences in the absorbance between the polymers is mainly due to the overall film thickness where PEDOT-maleimide and PEDOT-MA_cholesterol were not as thick of films as PEDOT.

Figure 13:
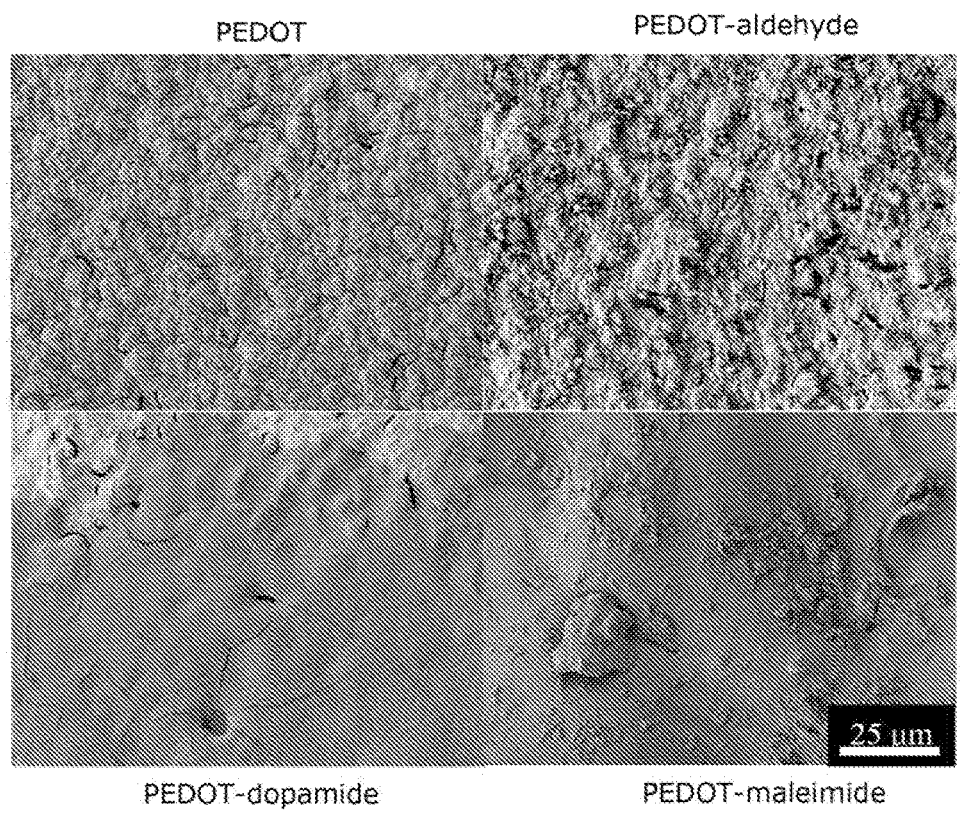
FIG. 13 shows SEM micrographs of electrodeposited PEDOT, PEDOT-aldehyde, PEDOT-dopamide, and PEDOT-maleimide, according to embodiments of the present invention.

FIG. 13 shows SEM micrographs of electrodeposited PEDOT, PEDOT-aldehyde, PEDOT-dopamide, and PEDOT-maleimide, according to embodiments of the present invention. PEDOT forms rough, bumpy structures that help increasing the surface area when it comes to electrical conductivity. PEDOT-aldehyde deviates from the normal PEDOT structure which gives it a similar morphology though in not as thick of a film. PEDOT-dopamide and PEDOT-maleimide have the competing characteristics of the attached functionality that cause smooth films with limited rough texture. These SEM micrographs show that the nature of functionality in the ADOT+ monomer can result in drastic differences in polymeric film morphologies which are partially responsible for and can affect the electrical response.

Thus, the above Examples show that biofunctional polythiophenes can be created from with biofunctional thiophene derivatives, and that the resulting biofunctional polymers are stable, and can be directly integrated with biomedical electronic devices.

What is claimed is:

1. A biofunctionalized 3,4-alkylenedioxythiophene monomer represented by a chemical formula $(C^1R^1R^2)(C^2R^3R^4)(C^3R^5R^6)_xO_2C_4H_2S$ (A'DOT+, where A' represents $C^1R^1R^2)(C^2R^3R^4)(C^3R^5R^6)_x$), wherein x=0 or 1, when x=0, the functionalized 3,4-alkylenedioxythiophene monomer is 3,4-ethylenedioxythiophene (E'DOT+; where E' represents $C^1R^1R^2)(C^2R^3R^4)$) and when x=1, the functionalized 3,4-alkylenedioxythiophene monomer is functionalized 3,4-propylenedioxythiophene (Pro'DOT+; where Pro' represents $C^1R^1R^2)(C^2R^3R^4)(C^3R^5R^6)$), wherein each of $R^1$, $R^2$, $R^3$, $R^4$, $R^5$, and $R^6$ is independently selected from hydrogen, a hydrocarbyl group, and a heteroatom-containing functional group, wherein one of $C^1$, $C^2$, or $C^3$ is bonded to an amide group, an ester group or a

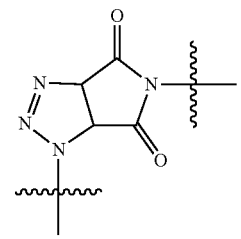 [SMILES: *N1C(=O)C2N=NN(*)C2C1=O]

group of a biofunctional hydrocarbyl moiety directly or through the hydrocarbyl group, and wherein the biofunctional hydrocarbyl moiety is selected from adamantane, L-cysteine hydrochloride, L-tyrosine, dopamine, tyramine, norepinephrine, 3-methoxytyramine, polyethylene glycol, and polyethylene glycol amine.

2. The biofunctionalized 3,4-alkylenedioxythiophene monomer according to claim 1 having one of the following structures:

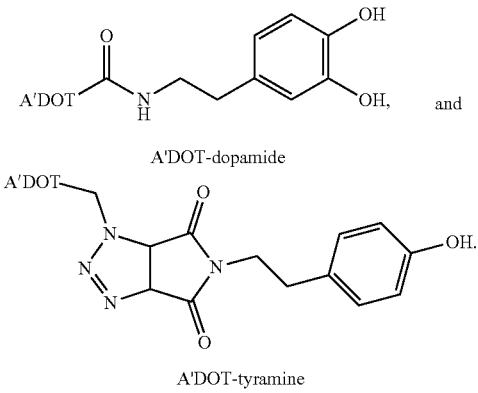

3. A method of making a functionalized polymer, the method comprising polymerizing at least one monomer in accordance with claim 1.

4. The method in accordance with claim 3, wherein the step of polymerizing comprises electropolymerizing.

5. An electronic biomedical device comprising the polymer of claim 3.

6. A functionalized polymer prepared by polymerization of at least one monomer in accordance with claim 1, wherein the functionalized polymer is represented by a chemical formula: $[(CR^1R^2)(CR^3R^4)(CR^5R^6)_xO_2C_4S]_m$, where m is a degree of polymerization and is in a range of 2 to 100.

7. A functionalized polymer prepared by copolymerization of at least one monomer in accordance with claim 1 and at least one additional monomer.

8. A biofunctionalized 3,4-alkylenedioxythiophene monomer represented by a chemical formula $(C^1R^1R^2)(C^2R^3R^4)(C^3R^5R^6)_xO_2C_4H_2S$ (A'DOT+, where A' represents $(CR^1R^2)(CR^3R^4)(CR^5R^6)_x$), wherein x=1, and the biofunctionalized 3,4-alkylenedioxythiophene monomer is functionalized 3,4-propylenedioxythiophene (Pro'DOT+; where Pro' represents $(C^1R^1R^2)(C^2R^3R^4)(C^3R^5R^6)$), wherein each of $R^1$, $R^2$, $R^3$, $R^4$, $R^5$, and $R^6$ is independently selected from hydrogen, a hydrocarbyl group, and a heteroatom-containing functional group, and wherein one of $C^1$, $C^2$, or $C^3$ is bonded to an amide group, an azide group, or an ester group of a biofunctional hydrocarbyl moiety directly or through the hydrocarbyl group.

9. The biofunctionalized 3,4-alkylenedioxythiophene monomer according to claim 8, wherein the biofunctional hydrocarbyl moiety is selected from adamantane, cholesterol, L-cysteine hydrochloride, L-tyrosine, dopamine, tyramine, norepinephrine, 3-methoxytyramine, polyethylene glycol, polyethylene glycol amine, and phospholipids.

10. The biofunctionalized 3,4-alkylenedioxythiophene monomer according to claim 8 having one of the following structures:

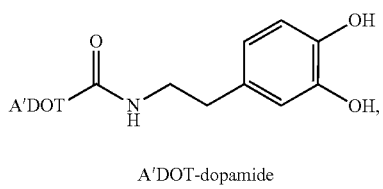

A'DOT-dopamide

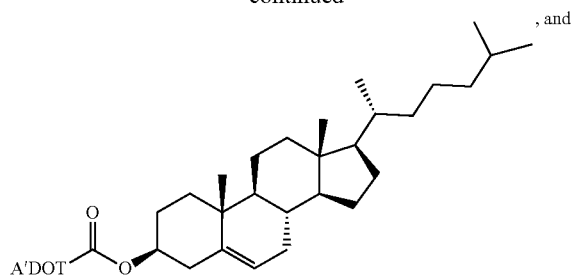

A'DOT-cholesterol

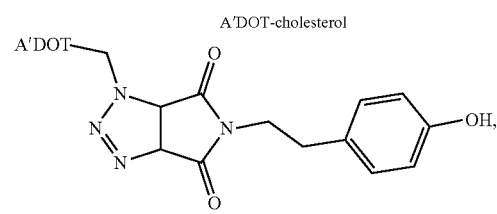

A'DOT-tyramine wherein A'DOT represents 3,4-propylenedioxythiophene (Pro'DOT).

11. A biofunctionalized 3,4-alkylenedioxythiophene monomer represented by a chemical formula $(C^1R^1R^2)(C^2R^3R^4)(C^3R^5R^6)_xO_2C_4H_2S$ (A'DOT+, where A' represents $C^1R^1R^2)(C^2R^3R^4)(C^3R^5R^6)_x$), wherein x=0 or 1, when x=0, the functionalized 3,4-alkylenedioxythiophene monomer is 3,4-ethylenedioxythiophene (E'DOT+; where E' represents $C^1R^1R^2)(C^2R^3R^4)$) and when x=1, the functionalized 3,4-alkylenedioxythiophene monomer is functionalized 3,4-propylenedioxythiophene (Pro'DOT+; where Pro' represents $C^1R^1R^2)(C^2R^3R^4)(C^3R^5R^6)$), wherein each of $R^1$, $R^2$, $R^3$, $R^4$, $R^5$, and $R^6$ is independently selected from hydrogen, a hydrocarbyl group, and a heteroatom-containing functional group, wherein one of $C^1$, $C^2$, or $C^3$ is bonded to an amide group or an ester group of a biofunctional hydrocarbyl moiety directly or through the hydrocarbyl group, and wherein the biofunctional hydrocarbyl moiety is selected from adamantane, L-cysteine hydrochloride, L-tyrosine, dopamine, tyramine, norepinephrine, 3-methoxytyramine, polyethylene glycol, and polyethylene glycol amine.

\* \* \* \* \*